(12) United States Patent
Hu et al.

(10) Patent No.: US 11,530,171 B2
(45) Date of Patent: Dec. 20, 2022

(54) METHOD TO PRODUCE C4 OLEFINS FROM NATURAL GAS-DERIVED ACETYLENE

(71) Applicant: West Virginia University, Morgantown, WV (US)

(72) Inventors: Jianli Hu, Morgantown, WV (US); Qingyuan Li, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 17/233,907

(22) Filed: Apr. 19, 2021

(65) Prior Publication Data

US 2021/0323893 A1 Oct. 21, 2021

Related U.S. Application Data

(60) Provisional application No. 63/012,488, filed on Apr. 20, 2020.

(51) Int. Cl.
| | |
|---|---|
| *C07C 2/40* | (2006.01) |
| *B01J 23/72* | (2006.01) |
| *B01J 23/46* | (2006.01) |
| *C07C 2/38* | (2006.01) |
| *C07C 11/08* | (2006.01) |
| *C07C 11/167* | (2006.01) |

(52) U.S. Cl.
CPC ............. *C07C 2/403* (2013.01); *B01J 23/462* (2013.01); *B01J 23/72* (2013.01); *C07C 2/38* (2013.01); *C07C 11/08* (2013.01); *C07C 11/167* (2013.01)

(58) Field of Classification Search
CPC .......... C07C 2/38; C07C 2/403; C07C 11/08; C07C 11/167; C07C 2521/08; C07C 2523/72; C07C 2529/24; C07C 2529/46; B01J 23/462; B01J 23/72; B01J 29/24; B01J 29/46; B01J 35/002
See application file for complete search history.

(56) References Cited

U.S. PATENT DOCUMENTS

| | | | |
|---|---|---|---|
| 2014/0058146 A1* | 2/2014 | Bricker | ..................... B01J 6/008 585/252 |
| 2019/0256442 A1* | 8/2019 | Schueth | ................. B01J 29/146 |

* cited by examiner

*Primary Examiner* — Ali Z Fadhel
(74) *Attorney, Agent, or Firm* — Innovators Legal

(57) ABSTRACT

In accordance with the purpose(s) of the present disclosure, as embodied and broadly described herein, the disclosure relates to a method for producing $C_4$ olefins from acetylene using supported metal-based catalysts and metal-based promoters. The method is inexpensive, efficient, and environmentally sound. Additionally, the method is selective for $C_4$ olefins and other value-added products based on changes to reaction parameters including temperature, feed gas composition, and promoter identity. This abstract is intended as a scanning tool for purposes of searching in the particular art and is not intended to be limiting of the present disclosure.

22 Claims, 18 Drawing Sheets

METHOD TO PRODUCE C4 OLEFINS FROM NATURAL GAS-DERIVED ACETYLENE

CROSS-REFERENCE TO RELATED APPLICATIONS

This application claims the benefit of U.S. Provisional Application No. 63/012,488, filed on Apr. 20, 2020, which is incorporated herein by reference in its entirety.

BACKGROUND $C_4$ olefins are produced from fluid-catalytic cracking (FCC), steam cracking of liquid hydrocarbon feedstock and/or of liquid petroleum gas, butane dehydrogenation, and other methods, and is typically carried out in petroleum refineries. Petroleum cracking processes typically involve high temperatures and are relatively energy-inefficient.

Demand for $C_4$ olefins is increasing due to industrial use of 1-butene, 2-butene, and butadiene as chemical intermediates. In particular, 1-butene and 2-butene can be used as feedstocks for alkylation reactions to produce trimethylpentanes, which are high-octane gasoline blending components, while butadiene is chiefly used as a monomer in the production of synthetic rubbers including styrene-butadiene rubber, polybutadiene rubber, nitrile rubbers, and chloroprene rubber. In the past decade, the demands for synthetic rubbers as well as for alkylate for use as a gasoline blending component continues to grow, particularly in emerging automotive industries in China, India, and Brazil, causing a shortage of $C_4$ olefins.

Catalytic conversion of hydrocarbons to make $C_4$ olefins is a primary focus of development in industrial processes. A one-step dehydration to convert ethanol into butadiene was developed in the 1930s (Lebedev process). A number of catalysts have been tested, and two catalyst systems ($Al_2O_3$/ZnO and $MgO/SiO_2$) appeared to be effective either in a pure form or doped with metal promoters. It has long been known that dehydrogenation reactions take place on the basic sites of magnesia and zinc oxide, while the dehydration step of the process occurs at acidic sites of silica and alumina. Various promoters including $K_2O$, $Na_2O$, CuO, Ag, and Au have been incorporated onto these catalysts in attempts to enhance the activity of the catalysts.

In addition to ethanol-based synthesis pathways, alternative paths to deliberate production of butadiene have been investigated. One such pathway was based on (deoxy) dehydration of polyols having $C_4$ backbones such as, for example, 1,3-, 2,3-, and 1,4-butanediols. For this process, a number of catalysts have been evaluated, including Na—P/$siO_2$, HZSM-5, $ThO_2$, and $Sc_2O_3$. However, high yields of undesired byproducts such as MEK and 3-buten-2-ol (3B2OL) were observed over acidic catalysts. Furthermore, n-butanol dehydration to 1-butene over oxides of Cr, Fe, and/or Al or of (Ca—Ni) phosphates has been evaluated. However, ethanol and polyol mutes to $C_4$ olefins is more expensive than production of these compounds from petroleum feedstocks.

Yet another method for producing $C_4$ olefins involves using ethylene from a natural gas feedstock. For example, 1-butene has been produced from ethylene dimerization over nickel-based catalysts, and $C_4$ olefins can be synthesized from hydrodimerization of acetylene, which can be accomplished via microwave or plasma-assisted methane conversion processes. Although acetylene can be synthesized with raw materials such as methane and ethane extracted from shale gas deposits, thus having a low impact on $CO_2$ emissions, past processes for the dimerization of acetylene to $C_4$ olefins have utilized Nieuwland catalysts consisting of CuCl/(KCl or $NH_4Cl$) to produce monovinylacetylene (MVA) olefin. However, these processes result in low acetylene conversion and low MVA selectivity. Furthermore, this process is typically carried out in liquid solution, where the presence of HCl is required for the reaction system in order to keep the catalysts stable, which could lead to the leaching of $CuCl_2$ into the environment.

Despite advances in $C_4$ olefin production research, there is still a scarcity of methods that are inexpensive, efficient, and selective for desired compounds while producing few undesired byproducts. Ideally, a new method for production would draw on an abundant raw material and contribute value-added byproducts. Additionally, a new method for production would be energy efficient and more environmentally sound than previous methods. These needs and other needs are satisfied by the present disclosure.

SUMMARY

In accordance with the purpose(s) of the present disclosure, as embodied and broadly described herein, the disclosure, in one aspect, relates to a method for producing $C_4$ olefins from acetylene using supported metal-based catalysts and metal-based promoters. The method is inexpensive, efficient, and environmentally sound. Additionally, the method is selective for $C_4$ olefins and other value-added products based on changes to reaction parameters including temperature, feed gas composition, and promoter identity.

In various aspects, disclosed herein are methods for producing $C_4$ olefins, the methods comprising: (a) placing a catalyst in a reactor; (b) providing a flow of feed gas through the reactor; (c) reacting the feed gas at a first temperature for a first period of time to produce a product mixture; and (d) collecting the product mixture; wherein the feed gas includes at least acetylene and the product mixture includes at least one $C_4$ olefin.

In a further aspect, disclosed herein are methods for producing $C_4$ olefins, the methods comprising: (a) placing a catalyst in a reactor; (b) providing a flow of feed gas through the reactor; (c) reacting the feed gas at a first temperature for a first period of time to produce a product mixture; and (d) collecting the product mixture; wherein the catalyst comprises a first metal; wherein the first metal is selected from Cu, Fe Co, Ni, Pd, Pt, Rh, and combinations thereof; wherein the catalyst further comprises a catalyst support; wherein the catalyst support is selected from comprises $SiO_2$, $Al_2O_3$, $ZrO_2$, $TiO_2$, a zeolite, ammonium zeolite mordenite, and combinations thereof; wherein the feed gas comprises acetylene; and wherein the product mixture comprises at least one $C_4$ olefin.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A shows a TEM image of a disclosed supported copper catalyst comprising 10 wt % $CuSiO_2$. FIG. 1B shows a TEM image of a disclosed supported copper catalyst comprising 10 wt % Cu/ZSM-5. FIG. 1C shows a TEM image of a disclosed supported copper catalyst comprising 10 wt % Cu/MOR. FIG. 1D shows representative XRD data for the disclosed Cu-based catalysts on different supports. FIG. 1E shows representative particle size distribution data determined using the TEM image of a disclosed supported copper catalyst comprising 10 wt % $CuSiO_2$ show in FIG. 1A. FIG. 1F shows representative particle size distribution data determined using the TEM image of a disclosed supported copper catalyst comprising 10 wt % Cu/ZSM-5 show in FIG. 1B. FIG. 1G shows representative particle size distribution data determined using the TEM image of a disclosed supported copper catalyst comprising 10 wt % Cu/MOR show in FIG. 1C.

FIG. 2A shows representative HrTPR for the indicated disclosed Cu-based catalysts. FIG. 2B shows representative $NH_3$-TPD for the indicated disclosed Cu-based catalysts.

FIG. 3A shows $C_2H_2$ conversions over different catalysts. FIG. 3B shows product selectivity over 10 wt % $Cu/SiO_2$ catalyst. FIG. 3C shows product selectivity over 10 wt % Cu/ZSM-5 catalyst. FIG. 3D shows product selectivity over 10 wt % Cu/MOR catalyst. Reaction conditions: $H_2:C_2H_2$=4:1 (molar ratio), 25 psig, WHSV=30,000 mL/g·h.

FIG. 4A shows a representative TEM image of a disclosed promoted copper catalyst comprising 1 wt % Ru with 10 wt % Cu/MOR. FIG. 4B shows a representative TEM image of a disclosed promoted copper catalyst comprising 1 wt % Ga with 10 wt % Cu/MOR. FIG. 4C shows a representative TEM image of a disclosed promoted copper catalyst comprising 1 wt % Ag with 10 wt % Cu/MOR. FIG. 4D shows a representative TEM image of a disclosed promoted copper catalyst comprising 1 wt % Pd with 10 wt % Cu/MOR. FIG. 4E shows representative XRD patterns for representative disclosed Cu-based catalysts as indicated therein.

FIG. 5 shows representative BET measurements for Cu-based catalysts as follows.

FIG. 7A 1 wt % Ru with 10 wt % Cu/MOR, FIG. 7B 1 wt % Ga with 10 wt % Cu/MOR, FIG. 7C 1 wt % Ag with 10 wt % Cu/MOR, FIG. 7D 1 wt % Pd with 10 wt % Cu/MOR. Reaction conditions: $H_2:C_2H_2$=4:1 (molar ratio), 25 psig, WHSV=36,000 mL/g·h.

FIG. 8A shows $H_2:C_2H_2$ molar ratio with reaction conditions 0 psig, 220° C., WHSV 36,000 mL/g·h. FIG. 8B shows reaction pressures with reaction conditions $H_2:C_2H_2$=4:1 (molar ratio), 220° C., WHSV=36,000 mL/g·h.

FIG. 10A shows time on stream of acetylene hydrogenation over 10% Cu/MOR catalyst with reaction conditions $H_2:C_2H_2$=4:1 (molar ratio), 220° C., 25 psig, WHSV=36,000 mL/g·h. FIG. 10B shows TEM morphology for the spent 10% Cu/MOR catalyst.

FIG. 10C shows an XRD pattern for the recycled 10% Cu/MOR catalyst. FIG. 10D shows Cu 2p XPS for the fresh and recycled 10% Cu/MOR catalyst.

Figure 1A:
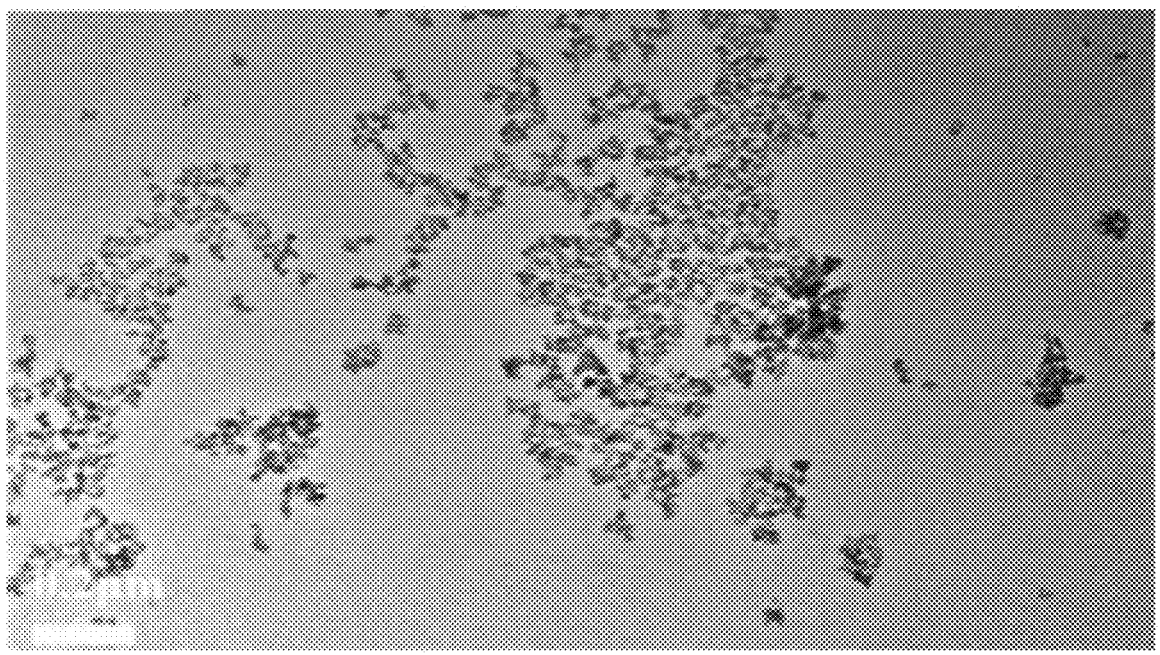
FIGS. 1A-1G show representative data relating to disclosed catalysts.
Figure 1B:
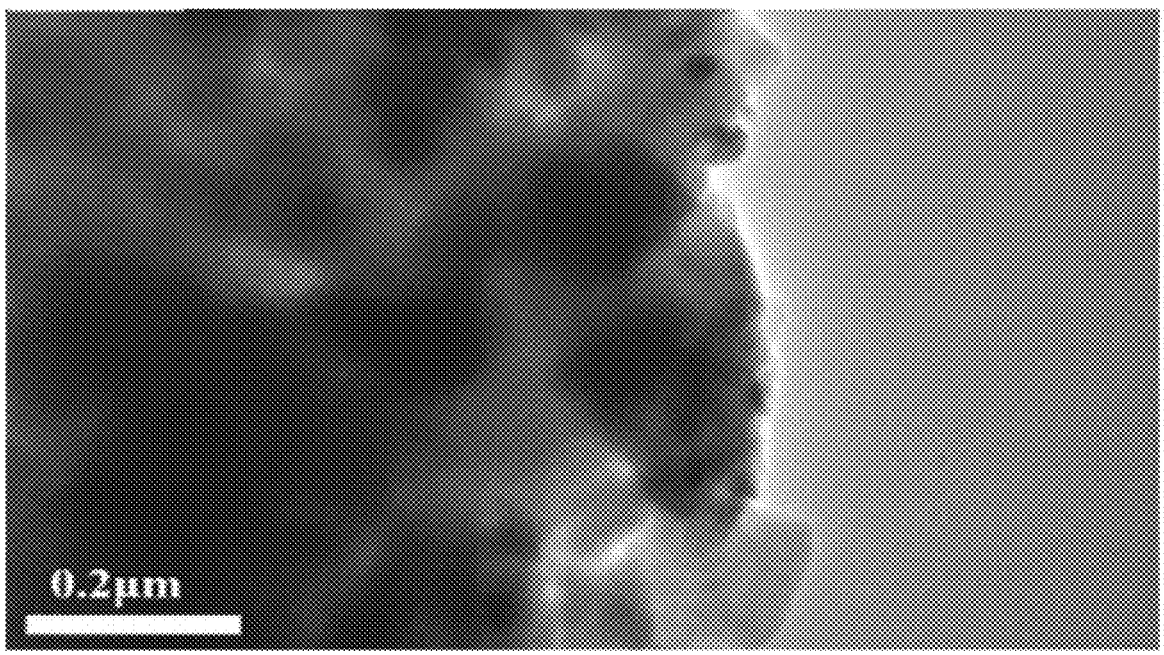

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a $C_4$ olefin," "a catalyst," or "a support," including, but not limited to, mixtures of two or more such $C_4$ olefins, catalysts, or supports, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', 'greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a promoter refers to an amount that is sufficient to achieve the desired improvement in the property modulated by the formulation component, e.g. achieving the desired level of selectivity for a particular given product. The specific level in terms of wt % in a composition required as an effective amount will depend upon a variety of factors including the amount and type of support, molar ratio of $H_2$ to $C_2H_2$, reaction temperature, and reaction pressure.

As used herein, the terms "optional" or "optionally" means that the subsequently described event or circumstance can or cannot occur, and that the description includes instances where said event or circumstance occurs and instances where it does not.

As used herein, "fluid catalytic cracking" or FCC is a conversion process conducted in petroleum refineries and is used to convert high molecular weight hydrocarbons from crude oil into more valuable, lower molecular weight products including, but not limited to, gasoline, olefins, and the like. FCC has been accomplished by thermal processes in the past, but is currently more often a catalytic process. In one aspect, gas byproducts of catalytic FCC possess more carbon-carbon double bonds, on average, than gas byproducts of thermal FCC.

"Steam cracking" is a conversion process used to convert saturated hydrocarbons into smaller hydrocarbons, which may be unsaturated. In one aspect, steam cracking is used for producing lighter alkenes or olefins. In a typical steam cracking reaction, a feedstock (e.g., naphtha, liquefied petroleum gas, ethane, propane, or butane) is thermally cracked using steam to produce lighter hydrocarbons. A typical steam cracking reaction may be conducted at 850° C., in the absence of oxygen.

Meanwhile, "butane dehydrogenation" reactions are conducted at temperatures of from 500-600° C. in the presence of catalysts. In these reaction, high purity products can be produced, but the catalysts are prone to coking and catalyst deactivation due to the high temperatures required; thus, the catalysts must be frequently regenerated, adding to the time and cost of the reaction.

"Temperature-programmed reduction" or TPR is a method for determining the most efficient conditions for reactions involving heterogeneous catalysts. In $H_2$-TPR, a catalyst precursor that is oxidized is subjected to a flow of reducing gas ($H_2$ in this instance, often mixed with an inert gas such as, for example, $N_2$) while temperature is slowly increased according to a programmed ramp. Gas composition exiting the container holding the catalyst precursor is monitored to determine optimum reaction conditions.

"Temperature-programmed desorption" or TPD is a technique useful for characterizing acid sites on oxide surfaces such as catalyst supports. $NH_3$-TPD uses ammonia, which, as a small molecule, can penetrate pores and cracks in a solid. In some aspects, $NH_3$-TPD can estimate the total number of available acid sites since it binds to weak, moderate, and strong acid sites, as well as both Bronsted and Lewis acid sites. Once ammonia has bound to the surface being analyzed, temperature is increased and an appropriate detector can monitor concentration of the desorbed species. In a further aspect, the temperature at which peaks desorb indicate acid site strength; e.g., a higher desorption temperature indicates stronger acid sites.

"Selectivity" as used herein refers to the ability of a given set of reaction conditions to produce comparatively more of a particular product (e.g., a given $C_4$ olefin) and less of any byproducts and/or undesired products.

The Barrett-Joyner-Halenda method ("BJH method") is useful for calculating pore sizes on a solid such as a catalyst. The BJH method is typically applied to mesopores (those with diameters of from about 2 to about 50 nm) through small macropores (with macropores having diameters >50 nm).

Unless otherwise specified, temperatures referred to herein are based on atmospheric pressure (i.e. one atmosphere).

Method for Producing $C_4$ Olefins

In various aspects, disclosed herein are methods for producing $C_4$ olefins, the methods comprising: (a) placing a catalyst in a reactor; (b) providing a flow of feed gas through the reactor; (c) reacting the feed gas at a first temperature for a first period of time to produce a product mixture; and (d) collecting the product mixture; wherein the feed gas includes at least acetylene and the product mixture includes at least one $C_4$ olefin.

In a further aspect, disclosed herein is a method for producing $C_4$ olefins, the method comprising: (a) placing a catalyst in a reactor; (b) providing a flow of feed gas through the reactor; (c) reacting the feed gas at a first temperature for a first period of time to produce a product mixture; and (d) collecting the product mixture; wherein the catalyst comprises a first metal; wherein the first metal is selected from Cu, Fe Co, Ni, Pd, Pt, Rh, and combinations thereof; wherein the catalyst further comprises a catalyst support; wherein the catalyst support is selected from comprises $SiO_2$, $Al_2O_3$, $ZrO_2$, $TiO_2$, a zeolite, ammonium zeolite mordenite, and combinations thereof; wherein the feed gas comprises acetylene; and wherein the product mixture comprises at least one $C_4$ olefin.

Catalyst Preparation

In one aspect, the catalysts disclosed herein can be synthesized using an incipient wetness technique. In a further aspect, the starting materials for catalyst synthesis can include nitrate salts and hydrates such as, for example, $Cu(NO_3)_2.2.5H_2O$, $NORu.3NO_3$, $Ga(NO_3)_3.xH_2O$, $Pd(NO_3)_2.2H_2O$, $AgNO_3$, or a combination thereof.

In a further aspect, once metals are introduced to the catalyst supports disclosed herein using the incipient wetness technique, the catalyst can be air dried at room temperature overnight and then dried further in an oven with heating at about 110° C. In a still further aspect, following air drying, the catalysts can be calcined at 550° C. for a period of from about 2 to about 6 hours, or for about 2, 3, 4, 5, or about 6 hours, or a combination of any of the foregoing values, or a range encompassing any of the foregoing values.

In a further aspect, the catalyst thus prepared can be reduced prior to use in the disclosed method. In one aspect, the catalyst can be reduced at 500° C. for 2 hours prior to use in the reactions disclosed herein. In a further aspect, the catalyst can be reduced under a gas flow. In one aspect, the catalyst can be reduced under hydrogen.

Catalysts and Supports

In a further aspect, in the method disclosed herein, the catalyst includes a first metal. In some aspects, the first metal can be copper. In any of these methods, the catalyst can further be contacted with a catalyst support. In one aspect, the catalyst support can be selected from $SiO_2$, $Al_2O_3$, $TiO_2$, $ZrO_2$, $CeO_2$, a zeolite, ammonium zeolite mordenite, another material, or a combination thereof. In some aspects, when the catalyst is a zeolite, it can be a ZSM zeolite, mordenite, or a combination thereof. In one aspect, when the catalyst is a ZSM zeolite, it can be ZSM-5.

In one aspect, the first metal can be present in an amount of from about 5 to about 15 wt % of the total weight of the catalyst and the catalyst support. In a further aspect, the first metal can be present in an amount of from about 7.5 to about 12.5 wt % of the total weight of the catalyst and the catalyst support. In a still further aspect, the first metal can be present in an amount of about 7.5, 8, 8.5, 9, 9.5, 10, 10.5, 11, 11.5, 12, or about 12.5 wt % of the total weight of the catalyst and the catalyst support, or a combination of any of the foregoing values, or a range encompassing any of the foregoing values. In one aspect, the first metal is about 10 wt % of the total weight of the catalyst and the catalyst support.

In any of these aspects, the catalyst can have a surface area of from about 200 to about 400 $m^2/g$, or of about 200, 225, 250, 275, 300, 325, 350, 375, or about 400 $m^2/g$, or a combination of any of the foregoing values, or a range encompassing any of the foregoing values. In another aspect, the catalyst can have an average pore volume of from about 0.05 to about 1.25 $cm^3/g$, or of about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.00, 1.05, 1.10, 1.15, 1.20, or about 1.25 $cm^3/g$, or a combination of any of the foregoing values, or a range encompassing any of the foregoing values. In still another aspect, the catalyst can have an average pore size of from about 15 to about 25 Å, or of about 15, 16, 17, 18, 19, 20, 21, 22, 23, 24, or about 25 Å, or a combination of any of the foregoing values, or a range encompassing any of the foregoing values.

Promoters

In one aspect, in the method disclosed herein, the catalyst can be further contacted with a promoter. In a further aspect, the promoter can be a second metal. In some aspects, the second metal can be ruthenium, gallium, silver, palladium, another metal, or a combination thereof. In any of these aspects, the promoter can be present in an amount of from about 0.5 to about 2 wt % of the total weight of the catalyst and the catalyst support. In a further aspect, the promoter can be present in an amount of from about 0.5 to about 1.5 wt % of the total weight of the catalyst and the catalyst support. In a further aspect, the promoter can be present in an amount of about 0.5, 0.6, 0.7, 0.8, 0.9, 1.0, 1.1, 1.2, 1.3, 1.4, or about 1.5 wt % of the total weight of the catalyst and the catalyst support, or a combination of any of the foregoing values, or a range encompassing any of the foregoing values. In one aspect, the promoter is present in an amount of about 1 wt % of the total weight of the catalyst and the catalyst support.

In one aspect, the first metal can be copper in an amount of about 10 wt % of the total weight of the catalyst and the catalyst support, the second metal can be ruthenium in an amount of about 1 wt % of the total weight of the catalyst and the catalyst support, and the catalyst support can be mordenite. Further in this aspect, the catalyst can have a surface are of from about 300 to about 350 $m^2/g$, or of about 300, 310, 320, 330, 340, or about 350 $m^2/g$, or a combination of any of the foregoing values, or a range encompassing any of the foregoing values. In another aspect, the catalyst can have an average pore volume of from about 0.05 to about 0.25 $cm^3/g$, or of about 0.05, 0.1, 0.15, 0.2, or about 0.25 $cm^3/g$, or a combination of any of the foregoing values, or a range encompassing any of the foregoing values. In still another aspect, the catalyst can have an average pore size of from about 20 to about 30 Å, or of about 20, 21, 22, 23, 24, 25, 26, 27, 28, 29, or about 30 Å, or a combination of any of the foregoing values, or a range encompassing any of the foregoing values.

In one aspect, the first metal can be copper in an amount of about 10 wt % of the total weight of the catalyst and the catalyst support, the second metal can be gallium in an amount of about 1 wt % of the total weight of the catalyst and the catalyst support, and the catalyst support can be mordenite. Further in this aspect, the catalyst can have a surface are of from about 300 to about 350 $m^2/g$, or of about 300, 310, 320, 330, 340, or about 350 $m^2/g$, or a combination of any of the foregoing values, or a range encompassing any of the foregoing values. In another aspect, the catalyst can have an average pore volume of from about 0.05 to about 0.20 $cm^3/g$, or of about 0.05, 0.1, 0.15, or about 0.20 $cm^3/g$, or a combination of any of the foregoing values, or a range encompassing any of the foregoing values. In still another aspect, the catalyst can have an average pore size of from about 20 to about 30 Å, or of about 20, 21, 22, 23, 24, 25, 26, 27, 28, 29, or about 30 Å, or a combination of any of the foregoing values, or a range encompassing any of the foregoing values.

In one aspect, the first metal can be copper in an amount of about 10 wt % of the total weight of the catalyst and the catalyst support, the second metal can be silver in an amount of about 1 wt % of the total weight of the catalyst and the catalyst support, and the catalyst support can be mordenite. Further in this aspect, the catalyst can have a surface are of from about 300 to about 400 $m^2/g$, or of about 300, 310, 320, 330, 340, 350, 360, 370, 380, 390, or about 400 $m^2/g$, or a combination of any of the foregoing values, or a range encompassing any of the foregoing values. In another aspect, the catalyst can have an average pore volume of from about 0.05 to about 0.25 $cm^3/g$, or of about 0.05, 0.1, 0.15, 0.2, or about 0.25 $cm^3/g$, or a combination of any of the foregoing values, or a range encompassing any of the foregoing values. In still another aspect, the catalyst can have an average pore size of from about 20 to about 30 Å, or of about 20, 21, 22, 23, 24, 25, 26, 27, 28, 29, or about 30 Å, or a combination of any of the foregoing values, or a range encompassing any of the foregoing values.

In one aspect, the first metal can be copper in an amount of about 10 wt % of the total weight of the catalyst and the catalyst support, the second metal can be palladium in an amount of about 1 wt % of the total weight of the catalyst and the catalyst support, and the catalyst support can be mordenite. Further in this aspect, the catalyst can have a surface are of from about 300 to about 400 $m^2/g$, or of about 300, 310, 320, 330, 340, 350, 360, 370, 380, 390, or about 400 $m^2/g$, or a combination of any of the foregoing values, or a range encompassing any of the foregoing values. In another aspect, the catalyst can have an average pore volume of from about 0.05 to about 0.20 $cm^3/g$, or of about 0.05, 0.1, 0.15, or about 0.20 $cm^3/g$, or a combination of any of the foregoing values, or a range encompassing any of the foregoing values. In still another aspect, the catalyst can have an average pore size of from about 20 to about 30 Å, or of about 20, 21, 22, 23, 24, 25, 26, 27, 28, 29, or about 30 Å, or a combination of any of the foregoing values, or a range encompassing any of the foregoing values.

Reactor and Feed Gas

In any of the disclosed aspects, the reactor can be a fixed-bed reactor or a moving bed reactor. In a further aspect, the feed gas can include acetylene, hydrogen, and a carrier gas.

In one aspect, the feed gas includes from about 7.5 to about 12.5 vol % acetylene. In a further aspect, the feed gas includes from about 7.5 to about 12.5 vol % acetylene. In a still further aspect, the feed gas can be about 7.5, 8, 8.5, 9, 9.5, 10, 10.5, 11, 11.5, 12, or about 12.5 vol % acetylene, or a combination of any of the foregoing values, or a range encompassing any of the foregoing values. In one aspect, the feed gas includes about 10 vol % acetylene.

In one aspect, the feed gas includes a molar ratio of hydrogen to acetylene of from about 2:1 to about 8:1, or of about 2:1, 3:1, 4:1, 5:1, 6:1, 7:1, or about 8:1, or a combination of any of the foregoing values, or a range encompassing any of the foregoing values. In one aspect, the molar ratio of hydrogen to acetylene in the feed gas is about 4:1.

In one aspect, the feed gas has a pressure of from about 0 to about 200 psig. In a further aspect, the feed gas has a pressure of from about 0 to about 100 psig. In a still furtheraspect, the feed gas has a pressure of from about 0 to about 50 psig. In one aspect, the feed gas has a pressure of from about 1 to about 200 psig. In a further aspect, the feed gas has a pressure of from about 1 to about 100 psig. In a still furtheraspect, the feed gas has a pressure of from about 1 to about 50 psig. In one aspect, the feed gas has a pressure of from about 10 to about 200 psig.

In a further aspect, the feed gas has a pressure of from about 10 to about 100 psig. In a still furtheraspect, the feed gas has a pressure of from about 10 to about 50 psig. In one aspect, the feed gas has a pressure of about 0, 5, 10, 15, 20, 25, 30, 35, 40, 45, 50, 55, 60, 65, 70, 75, 80, 85, 90, 95, or about 100 psig, or a combination of any of the foregoing values, or a range encompassing any of the foregoing values.

In one aspect, the feed gas has a weight hourly space velocity (WHSV) of from about 123,500 to about 50,000 mL/g·h. In a still further aspect, the feed gas has a weight hourly space velocity (WHSV) of from about 24,000 to about 40,000 mL/g·h. In a yet further aspect, the feed gas has a weight hourly space velocity (WHSV) of from about 30,000 to about 36,000 mL/g·h. In a yet further aspect, the feed gas has a weight hourly space velocity (WHSV) of about 30,000, 31,000, 32,000, 33,000, 34,000, 35,000, or about 36,000 mL/g·h, or a combination of any of the foregoing values, or a range encompassing any of the foregoing values. In one aspect, the WHSV is about 36,000 mL/g·h.

Reaction Time and Temperature

In one aspect, the first temperature is from about 100° C. to about 400° C. In a further aspect, the first temperature is from about 100° C. to about 360° C. In a still further aspect, the first temperature is from about 100° C. to about 300° C. In a yet further aspect, the first temperature is from about 100° C. to about 260° C. In one aspect, the first temperature is from about 150° C. to about 400° C. In a further aspect, the first temperature is from about 150° C. to about 360° C. In a still further aspect, the first temperature is from about 150° C. to about 300° C. In a yet further aspect, the first temperature is from about 150° C. to about 260° C. In one aspect, the first temperature is from about 160° C. to about 400° C. In a further aspect, the first temperature is from about 160° C. to about 360° C. In a still further aspect, the first temperature is from about 160° C. to about 300° C. In a yet further aspect, the first temperature is from about 160° C. to about 260° C. In one aspect, the first temperature is about 180, 185, 190, 195, 200, 205, 210, 215, 220, 225, 230, 235, 240, 245, 250, 255, or about 260° C., or a combination of any of the foregoing values, or a range encompassing any of the foregoing values. In one aspect, the first temperature is about 220° C.

Product Gas Mixture

In one aspect, the at least one $C_4$ olefin produced by the disclosed method can be 1-butene, cis-2-butene, trans-2-butene, 1,3-butadiene, or a combination thereof. In a further aspect, the product mixture can include at least 50 mol % $C_4$ olefin, at least 60 mol % $C_4$ olefin, at least 70 mol % $C_4$ olefin, at least 80 mol % $C_4$ olefin, at least 85 mol % $C_4$ olefin, or at least 90 mol % $C_4$ olefin, or a combination of any of the foregoing values, or a range encompassing any of the foregoing values.

In some aspects, the product gas mixture includes at least one value-added product. In a further aspect, the value-added product can be ethylene, benzene, another product, or a combination thereof. In one aspect, the value-added product can be benzene. Further in this aspect, when the value-added product is benzene, the product mixture can include from about 3 to about 8 mol % benzene, or can include 3, 4, 5, 6, 7, or about 8 mol % benzene, or a combination of any of the foregoing values, or a range encompassing any of the foregoing values. In another aspect, the value-added product can be ethylene. Further in this aspect, the product mixture can include from about 5 to about 25 mol % ethylene, or about 5, 10, 15, 20, or about 25 mol % ethylene, or a combination of any of the foregoing values, or a range encompassing any of the foregoing values.

Catalyst Regeneration

In any of the aspects disclosed herein, the catalyst can be regenerated following performance of the method. In one aspect, following regeneration of the catalyst, the method can be performed again using the same catalyst. In a further aspect, the catalyst can be regenerated at least 2 times, at least 5 times, at least 10 times, or more, or a combination of any of the foregoing values, or a range encompassing any of the foregoing values. In any of these aspects, product yields are comparable for regenerated catalyst and freshly-prepared catalyst.

In one aspect, disclosed herein is a composition including at least one hydrocarbon produced by the disclosed method and/or an article including or made in part from the composition.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

REFERENCES

References are cited herein throughout using the format of reference number(s) enclosed by parentheses corresponding to one or more of the following numbered references. For example, citation of references numbers 1 and 2 immediately herein below would be indicated in the disclosure as (Refs. 1 and 2).

1. M. Bender, ChemBioEng Reviews 2014, 1, 136-147.
2. G. Pomalaza, M. Capron, V. Ordomsky, F. Dumeignil, Catalysts 2016, 6, 203.
3. Z. Xu, J. P. Chada, L. Xu, D. Zhao, D. C. Rosenfeld, J. L. Rogers, I. Hermans, M. Mavrikakis, G. W. Huber, ACS Catal. 2018, 8, 2488-2497.
4. G. O. Ezinkwo, V. P. Tretyakov, A. Aliyu, A. M. llolov, ChemBioEng Reviews 2014, 1, 194-203.
5. M. D. Jones, C. G. Keir, C. Di lulio, R. A. Robertson, C. V. Williams, D. C. Apperley, Catal. Sci. Technol. 2011, 1, 267-272.
6. S. Kvisle, A. Aguero, R. P. A. Sneeden, Appl. Catal. 1988, 43, 117-131.
7. Y. Kitayama, M. Satoh, T. Kodama, Catal. Lett. 1996, 36, 95-97.
8. R. Ohnishi, T. Akimoto, K. Tanabe, J. Chem. Soc., Chem. Commun. 1985, 1613-1614.
9. M. Galbe, G. Zacchi, Appl. Microbiol. Biotechnol. 2002, 59, 618-628.

10. E. V. Makshina, W. Janssens, B. F. Sels, P. A. Jacobs, Catal. Today 2012, 198, 338-344.
11. V. Bro§ teanu, I. Banu, G. Bozga, B. Romanian Chem. Eng. Soc. 2018, 5 2-27.
12. H. Duan, Y. Yamada, S. Sato, Chem. Lett. 2016, 45, 1036-1047.
13. W. Kim, W. Shin, K. J. Lee, H. Song, H. S. Kim, D. Seung, I. N. Filimonov, Appl. Catal. A: Gen. 2016, 511, 156-167.
14. Q. Zheng, M. D. Wales, M. G. Heidlage, M. Rezac, H. Wang, S. H. Bossmann, K. L. Hohn, J. catal. 2015, 330, 222-237.
15. M. E. Winfield, Australian Journal of Chemistry 1950, 3, 290-305.
16. H. Duan, Y. Yamada, S. Sato, Appl. Catal. A: Gen. 2015, 491, 163-169.
17. E. V. Makshina, M. Dusselier, W. Janssens, J. Degreve, P. A. Jacobs, B. F. Sels, Chem. Soc. Rev. 2014, 43, 7917-7953.
18. R. M. West, D. J. Braden, J. A. Dumesic, J. Catal. 2009, 262, 134-143.
19. R. Beucher, R. D. Andrei, C. Cammarano, A. Galameau, F. Fajula, V. Hulea, ACS Catal. 2018, 8, 3636-3640.
20. E. D. Metzger, C. K. Brozek, R. J. Comito, M. Dinci, ACS central sci. 2016, 2, 148-153.
21. V. Hulea, ACS Catal. 2018, 8, 3263-3279.
22. M. H. Kwon, J. S. Yoon, M. Lee, D. W. Hwang, Y. Kim, M. B. Park, H. J. Chae, Appl. Catal. A: Gen. 2019, 572, 226-231.
23. T. Li, C. Rehmet, Y. Cheng, Y. Jin, Y. Cheng, Plasma Chem. and Plasma Process 2017, 37, 1033-1049.
24. M. Heintze, M. Magureanu, J. appl. phys. 2002, 92, 2276-2283.
25. D. K. Dinh, D. H. Lee, Y. H. Song, S. Jo, K. T. Kim, M. Iqbal, H. Kang, RSC Advances 2019, 9, 32403-32413.
26. J. Happel, L. Kramer, Selective pyrolysis of methane to acetylene and hydrogen, US, U.S. Pat. No. 3,156,733A. 1964-11-10.
27. J. Liu, Y. Zuo, M. Han, Z. Wang, J. Chem. Technol. Biotechnol. 2013, 88, 408-414.
28. Y. You, J. Luo, J. Xie, B. Dai, Catalysts 2017, 7, 394.
29. M. H. Mahyuddin, T. Tanaka, A. Staykov, Y. Shiota, K. Yoshizawa, Inorg. chem. 2018, 57, 10146-10152.
30. D. K. Pappas, A. Martini, M. Dyballa, K. Kvande, S. Teketel, K. A. Lomachenko, R. Baran, P. Glatzel, B. Arstad, G. Berlier, C. Lamberti, J. Am. Chem. Soc. 2018, 140, 15270-15278.
31. Y. Chu, B. Han, A. Zheng, X. Yi, F. Deng, J. Phys. Chem. C 2013, 117, 2194-2202.
32. M. Zhang, S. Xu, Y. Wei, J. Li, J. Chen, J. Wang, W. Zhang, S. Gao, X. Li, C. Wang, Z. Liu, RSC Adv. 2016, 6, 95855-95864.
33. K. Wang, X. Dong, C. Zhao, X. Qian, Y. Xu, Electrochimica Acta 2015, 152, 433-442.
34. X. Cao, A. Mirjalili, J. Wheeler, W. Xie, B. W. L. Jang, Front. Chem. Sci. Eng. 2015, 9, 442-449.
35. Q. Dai, Q. Zhu, Y. Lou, X. Wang, J. catal. 2018, 357, 29-40.
36. T. Zhang, J. Liu, D. Wang, Z. Zhao, Y. Wei, K. Cheng, G. Jiang, A. Duan, Appl. Catal. B: Environ. 2014, 148, 520-531.
37. B. Dou, G. Lv, C. Wang, Q. Hao, K. Hui, Chem. Eng. J. 2015, 270, 549-556.
38. X. Cao, T. Lyu, W. Xie, A. Mirjalili, A. Bradicich, R. Huitema, B. W. L. Jang, J. K. Keum, K. More, C. Liu, X. Yan, Front. Chem. Sci. Eng. 2019 1-12.
39. W. P. Dow, Y. P. Wang, T. J. Huang, Appl. Catal. A: Gen. 2000, 190, 25-34.
40. M. Wang, S. Huang, J. Lb, Z. Cheng, Y. Li, S. Wang, X. Ma, Chin. J. Catal. 2016, 37, 1530-1537.
41. X. Xing, N. Li, Y. Sun, G. Wang, J. Cheng, Z. Hao, Catal. Today 2020, 339, 192-199.
42. J. Liu, F. Yu, J. Liu, L. Cui, Z. Zhao, Y. Wei, Q. Sun, J. Environ. Sci. 2016, 48, 45-58.
43. N. E. U. S. Blanch-Raga, A. E. Palomares, J. Martinez-Triguero, S. Valencia, Appl. Catal. B: Environ. 2016, 187, 90-97.
44. C. Li, J. Luo, Q. Zhang, J. Xie, J. Zhang, B. Dai, New J. Chem. 2019, 43, 13608-13615.
45. J. Liu, Y. Zuo, M. Han, Z. Wang, D. Wang, J. Natural Gas Chem. 2012, 21, 495-500.
46. F. Studt, F. Abild-Pedersen, T. Bligaard, R. Z. Serensen, C. H. Christensen, J. K. Norskov, Science 2008, 320, 1320-1322.
47. F. Studt, F. Abild-Pedersen, T. Bligaard, R. Z. Serensen, C. H. Christensen, J. K. Norskov, Angew. Chem. Int. Ed. 2008, 47, 9299-9302.
48. Q. Li, Y. Wang, G. Skoptsov, J. Hu, Ind. Eng. Chem. Res. 2019, 58, 20620-20629.
49. F. Maleki, P. Schlexer, G. Pacchioni, Surface Sci. 2018, 668, 125-133.
50. A. Serkeny, React. Kinet. Catal. Lett. 2001, 74, 299-307.
51. J. Dou, Y. Sheng, C. Choong, L. Chen, H. C. Zeng, Appl. Catal. B: Environ. 2017, 219, 580-591.
52. X. Yang, Y. Su, W. Qian, M. Yuan, H. Zhou, W. Deng, B. Zhao, J. Fuel Chem. Technol. 2017, 45, 1365-1375.
53. J. Xiong, X. Dong, L. Li, J. Natural Gas Chem. 2012, 21, 445-451.
54. H. Romar, A. H. Lillebo, P. Tynjifi, T. Hu, A. Holmen, E. A. Blekkan, U. Lassi, J. Mater. Sci. Res. 2016, 5, 33-43.
55. Y. Wang, M. Peng, C. Ye, C. Gan, J. Zhang, C. Guo, Appl. Organometal. Chem. 2019, 33, e5076.
56. Q. Yang, D. Wang, C. Wang, K. Li, Y. Peng, J. Li, ChemCatChem 2018, 10, 4838-4843.
57. X. Zhang, H. Dong, D. Zhao, Y. Wang, Y. Wang, L. Cui, Chem. Res. Chin. Univ. 2016, 32.
58. X. Zhang, H. Dong, Y. Wang, N. Liu, Y. Zuo, L. Cui, Chem. Eng. J. 2016, 283, 1097-1107.
59. S. Mhadmhan, A. Franco, A. Pineda, P. Reubroycharoen, R. Luque, ACS Sustainable Chem. Eng. 2019, 7, 14210-14216.
60. G. B. Kasar, R. Medhekar, P. N. Bhosale, C. V. Rode, Ind. Eng. Chem. Res. 2019, 58, 19803-19817.
61. E. Karakhanov, A. Maximov, A. Zolotukhina, A. Mamadli, A. Vutolkina, A. Ivanov, Catalysts 2017, 7, 86.
62. J. Osswald, R. Giedigkeit, R. E. Jentoft, M. Armbrister, F. Girhsdies, K. Kovnir, T. Ressler, Y. Grin, R. Schlögl, J. catal. 2008, 258, 210-218.
63. C. Li, Y. Chen, S. Zhang, J. Zhou, F. Wang, S. He, M. Wei, D. G. Evans, X. Duan, ChemCatChem 2014, 6, 824-831.
64. Y. He, Y. Liu, P. Yang, Y. Du, J. Feng, X. Cao, J. Yang, D. Li, J. catal. 2015, 330, 61-70.
65. Y. Liu, J. Zhao, Y. He, J. Feng, T. Wu, D. Li, J. catal. 2017, 348, 135-145.
66. W. G. Menezes, L. Altmann, V. Zielasek, K. Thiel, M. Baumer, J. catal. 2013, 300, 125-135.
67. A. J. McCue, A. M. Shepherd, A. A. James, Catal. Sci. Technol. 2015, 5, 2880-2890.
68. T. Tachiyama, M. Yoshida, T. Aoyagi, S. Fukuzumi, Appl. Organometal. Chem. 2008, 22, 205-210.
69. T. Tachiyama, M. Yoshida, T. Aoyagi, S. Fukuzumi, Chem. Lett. 2007, 37, 38-39.

70. K. Judai, A. S. Wörz, S. Abbet, J. M. Antonietti, U. Heiz, A. Del Vitto, L. Giordano, G. Pacchioni, Phys. Chem. Chem. Phys. 2005, 7, 955-962.
71. G. Pacchioni, R. M. Lambert, Surf. Sci. 1994, 304, 208-222.
72. T. Ghodselahi, M. A. Vesaghi, A. Shafiekhani, A. Baghizadeh, M. Lameii, Appl. Surf. Sci. 2008, 255, 2730-2734.
73. X. Liu, X. Wu, D. Weng, L. Shi, J. Rare Earth. 2016, 34, 1004-1009.

Aspects

The following listing of exemplary aspects supports and is supported by the disclosure provided herein.

Aspect 1. A method for producing C4 olefins from acetylene, the method comprising: (a) placing a catalyst in a reactor; (b) providing a flow of feed gas through the reactor; (c) reacting the feed gas at a first temperature for a first period of time to produce a product mixture; and (d) collecting the product mixture; wherein the feed gas comprises acetylene and the product mixture comprises at least one C4 olefin.

Aspect 2. The method of Aspect 1, wherein the catalyst comprises a first metal.

Aspect 3. The method of Aspect 2, wherein the first metal comprises Cu, Fe Co, Ni, Pd, Pt, Rh.

Aspect 4. The method of Aspect 3, wherein the first metal comprises Cu.

Aspect 5. The method of any one of Aspect 1-Aspect 4, wherein the catalyst further comprises a catalyst support.

Aspect 6. The method of Aspect 5, wherein the catalyst support comprises $SiO_2$, $Al_2O_3$, $ZrO_2$, $TiO_2$, $CeO_2$, a zeolite, ammonium zeolite mordenite, or a combination thereof.

Aspect 7. The method of Aspect 5 or Aspect 6, wherein the zeolite comprises a ZSM zeolite, USY-Zeolite, mordenite, or a combination thereof.

Aspect 8. The method of Aspect 7, wherein the ZSM zeolite comprises ZSM-5.

Aspect 9. The method of any one of Aspect 5-Aspect 8, wherein the first metal comprises copper in an amount of from about 1 to about 30 wt % of the total weight of the catalyst and the catalyst support.

Aspect 10. The method of any one of Aspect 5-Aspect 8, wherein the first metal comprises copper in an amount of from about 7.5 to about 12.5 wt % of the total weight of the catalyst and the catalyst support.

Aspect 11. The method of any one of Aspect 5-Aspect 8, wherein the first metal comprises copper in an amount of about 10 wt % of the total weight of the catalyst and the catalyst support.

Aspect 12. The method of any one of Aspect 5-Aspect 11, wherein the catalyst comprises a surface area of from about 100 to about 400 $m^2/g$.

Aspect 13. The method of any one of Aspect 5-Aspect 11, wherein the catalyst comprises a surface area of from about 200 to about 400 $m^2/g$ Aspect 14. The method of any one of Aspect 5-Aspect 11, wherein the catalyst comprises a pore volume of from about 0.05 to about 1.25 $cm^3/g$.

Aspect 15. The method of any one of Aspect 5-Aspect 11, wherein the catalyst comprises an average pore size of from about 5 to about 100 Å

Aspect 16. The method of any one of Aspect 5-Aspect 11, wherein the catalyst comprises an average pore size of from about 15 to about 25 Å.

Aspect 17. The method of any one of Aspect 1-Aspect 16, wherein the catalyst further comprises a promoter.

Aspect 18. The method of Aspect 17, wherein the promoter comprises a second metal.

Aspect 19. The method of Aspect 18, wherein the second metal comprises ruthenium, gallium, silver, palladium, rhodium, platinum, cobalt, or a combination thereof.

Aspect 20. The method of any one of Aspect 17-Aspect 19, wherein the promoter is present in an amount of from about 0.05 to about 10 wt % of the total weight of the catalyst and the catalyst support.

Aspect 21. The method of any one of Aspect 17-Aspect 19, wherein the promoter is present in an amount of from about 0.5 to about 1.5 wt % of the total weight of the catalyst and the catalyst support.

Aspect 22. The method of any one of Aspect 17-Aspect 19, wherein the promoter is present in an amount of about 1 to 3 wt % of the total weight of the catalyst and the catalyst support.

Aspect 23. The method of any one of Aspect 17-Aspect 19, wherein the promoter is present in an amount of about 1 wt % of the total weight of the catalyst and the catalyst support.

Aspect 24. The method of any one of Aspect 19-Aspect 23, wherein the first metal comprises copper in an amount of 10 wt % of the total weight of the catalyst and the catalyst support, the second metal comprises ruthenium in an amount of from about 0.1 wt % to about 1 wt % of the total weight of the catalyst and the catalyst support, and the catalyst support comprises mordenite.

Aspect 25. The method of Aspect 24, wherein the catalyst comprises a surface area of from about 250 to about 350 $m^2/g$.

Aspect 26. The method of Aspect 24, wherein the catalyst comprises a surface area of from about 300 to about 350 $m^2/g$.

Aspect 27. The method of Aspect 24, wherein the catalyst comprises a pore volume of from about 0.05 to about 0.25 $cm^3/g$.

Aspect 28. The method of Aspect 24, wherein the catalyst comprises a pore volume of from about 0.05 to about 1.0 $cm^3/g$.

Aspect 29. The method of Aspect 24, wherein the catalyst comprises an average pore size of from about 20 to about 50 Å.

Aspect 30. The method of Aspect 24, wherein the catalyst comprises an average pore size of from about 20 to about 30 Å.

Aspect 31. The method of any one of Aspect 19-Aspect 23, wherein the first metal comprises copper in an amount of 10 wt % of the total weight of the catalyst and the catalyst support, the second metal comprises gallium in an amount of 1 wt % of the total weight of the catalyst and the catalyst support, and the catalyst support comprises mordenite.

Aspect 32. The method of Aspect 31, wherein the catalyst comprises a surface area of from about 250 to about 400 $m^2/g$.

Aspect 33. The method of Aspect 31, wherein the catalyst comprises a surface area of from about 300 to about 350 $m^2/g$.

Aspect 34. The method of Aspect 31, wherein the catalyst comprises a pore volume of from about 0.05 to about 1.0 $cm^3/g$.

Aspect 35. The method of Aspect 31, wherein the catalyst comprises a pore volume of from about 0.05 to about 0.20 $cm^3/g$.

Aspect 36. The method of Aspect 31, wherein the catalyst comprises an average pore size of from about 10 to about 50 Å.

Aspect 37. The method of Aspect 31, wherein the catalyst comprises an average pore size of from about 20 to about 30 Å.

Aspect 38. The method of any one of Aspect 19-Aspect 23, wherein the first metal comprises copper in an amount of 10 wt % of the total weight of the catalyst and the catalyst support, the second metal comprises silver in an amount of 1 wt % of the total weight of the catalyst and the catalyst support, and the catalyst support comprises mordenite.

Aspect 39. The method of clam Aspect 38, wherein the catalyst comprises a surface area of from about 300 to about 400 m$^2$/g.

Aspect 40. The method of clam Aspect 38, wherein the catalyst comprises a pore volume of from about 0.05 to about 1.0 cm$^3$/g.

Aspect 41. The method of clam Aspect 38, wherein the catalyst comprises a pore volume of from about 0.05 to about 0.25 cm$^3$/g.

Aspect 42. The method of clam Aspect 38, wherein the catalyst comprises an average pore size of from about 5 to about 50 Å.

Aspect 43. The method of clam Aspect 38, wherein the catalyst comprises an average pore size of from about 20 to about 30 Å.

Aspect 44. The method of any one of Aspect 19-Aspect 23, wherein the first metal comprises copper in an amount of 10 wt % of the total weight of the catalyst and the catalyst support, the second metal comprises palladium in an amount of 1 wt % of the total weight of the catalyst and the catalyst support, and the catalyst support comprises mordenite.

Aspect 45. The method of clam Aspect 44, wherein the catalyst comprises a surface area of from about 300 to about 400 m$^2$/g.

Aspect 46. The method of clam Aspect 44, wherein the catalyst comprises a pore volume of from about 0.05 to about 1.0 cm$^3$/g.

Aspect 47. The method of clam Aspect 44, wherein the catalyst comprises a pore volume of from about 0.05 to about 0.20 cm$^3$/g.

Aspect 48. The method of clam Aspect 44, wherein the catalyst comprises an average pore size of from about 5 to about 50 Å.

Aspect 49. The method of clam Aspect 44, wherein the catalyst comprises an average pore size of from about 20 to about 30 Å.

Aspect 50. The method of any one of Aspect 1-Aspect 39, wherein the reactor comprises a fixed-bed reactor, fluidized-bed reactor or a moving bed reactor.

Aspect 51. The method of any one of Aspect 1-Aspect 45, wherein the feed gas comprises acetylene and hydrogen.

Aspect 52. The method of Aspect 51, wherein the feed gas comprises from about 5 to about 95 vol % acetylene.

Aspect 53. The method of Aspect 51, wherein the feed gas comprises from about 7.5 to about 12.5 vol % acetylene.

Aspect 54. The method of any one of Aspect 51-Aspect 53, wherein the feed gas comprises a molar ratio of hydrogen to acetylene of from about 2:1 to about 8:1.

Aspect 55. The method of any one of Aspect 51-Aspect 53, wherein the feed gas comprises a molar ratio of hydrogen to acetylene of about 4:1.

Aspect 56. The method of any one of Aspect 1-Aspect 55, wherein the feed gas comprises a pressure of from about 0 to about 1000 psig.

Aspect 57. The method of any one of Aspect 1-Aspect 55, wherein the feed gas comprises a pressure of from about 0 to about 100 psig.

Aspect 58. The method of any one of Aspect 1-Aspect 55, wherein the feed gas comprises a pressure of about 25-100 psig.

Aspect 59. The method of any one of Aspect 1-Aspect 55, wherein the feed gas comprises a pressure of about 25 psig.

Aspect 60. The method of any one of Aspect 1-Aspect 59, wherein the feed gas comprises a weight hourly space velocity (WHSV) of from about 5,000 mL/g·H to about 100,000 mL/g·h.

Aspect 61. The method of any one of Aspect 1-Aspect 59, wherein the feed gas comprises a weight hourly space velocity (WHSV) of from about 30,000 mL/g·H to about 36,000 mL/g·h.

Aspect 62. The method of any one of Aspect 1-Aspect 59, wherein the feed gas comprises a weight hourly space velocity (WHSV) of about 36,000 mL/g·h.

Aspect 63. The method of any one of Aspect 1-Aspect 62, wherein the first temperature is from about 150° C. to about 400° C.

Aspect 64. The method of any one of Aspect 1-Aspect 62, wherein the first temperature is from about 200° C. to about 300° C.

Aspect 65. The method of any one of Aspect 1-Aspect 62, wherein the first temperature is from about 180° C. to about 260° C.

Aspect 66. The method of any one of Aspect 1-Aspect 62, wherein the first temperature is about 220° C.

Aspect 67. The method of any one of Aspect 1-Aspect 66, wherein the at least one C4 olefin comprises 1-butene, cis-2-butene, trans-2-butene, 1,3-butadiene, or a combination thereof.

Aspect 68. The method of any one of Aspect 1-Aspect 67, wherein the product mixture comprises at least 50 mol % C4 olefins.

Aspect 69. The method of any one of Aspect 1-Aspect 67, wherein the product mixture comprises at least 60 mol % C4 olefins.

Aspect 70. The method of any one of Aspect 1-Aspect 67, wherein the product mixture comprises at least 70 mol % C4 olefins.

Aspect 71. The method of any one of Aspect 1-Aspect 67, wherein the product mixture comprises at least 80 mol % C4 olefins.

Aspect 72. The method of any one of Aspect 1-Aspect 67, wherein the product mixture comprises at least 85 mol % C4 olefins.

Aspect 73. The method of any one of Aspect 1-Aspect 67, wherein the product mixture comprises at least 90 mol % C4 olefins.

Aspect 74. The method of any one of Aspect 1-Aspect 73, wherein the product mixture further comprises at least one value-added product.

Aspect 75. The method of Aspect 74, wherein the at least one value-added product comprises ethylene, benzene, or a combination thereof.

Aspect 76. The method of Aspect 75, wherein the product mixture comprises from about 3 mol % to about 8 mol % benzene.

Aspect 77. The method of Aspect 75, wherein the product mixture comprises from about 5 mol % to about 25 mol % ethylene.

Aspect 78. The method of any one of Aspect 1-Aspect 77, further comprising regenerating the catalyst following performance of the method.

Aspect 79. The method of Aspect 78, wherein following regenerating the catalyst, the method can be performed again.

Aspect 80. A composition comprising a hydrocarbon produced by the method of any one of Aspect 1-Aspect 79.

Aspect 81. An article comprising the composition of Aspect 80.

From the foregoing, it will be seen that aspects herein are well adapted to attain all the ends and objects hereinabove set forth together with other advantages which are inherent to the structure and/or within the scope of the present disclosure as could be inferred from an understanding thereof.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Catalyst Synthesis

The Cu-based catalysts were synthesized by incipient wetness technique. The chemicals used in the synthesis include $Cu(NO_3)_2 \cdot 2.5H_2O$ (Alfa Aesar), $NORu-3NO_3$ (Alfa Aesar), $Ga(NO_3)_3 \cdot xH_2O$ (Alfa Aesar), $Pd(NO_3)_2 \cdot 2H_2O$ (Sigma-Aldrich), $AgNO_3$ (Sigma-Aldrich), $SiO_2$ (CAB-O-SIL EH-5, CABOT), ZSM-5 (CBV2314, Zeolyst), ammonium zeolite mordenite (20:1 mole ratio $SiO_2:Al_2O_3$, Alfa Aesar, noted as MOR). In a typical synthesis procedure, m(Cu)/m(support) was set at 10 wt %, whereas the content of Ru, Ag, Ga and Pd was fixed at 1 wt %. After introducing metals by incipient wetness technique, samples were air dried at room temperature overnight then continued dried in an oven at 110° C. overnight. The obtained samples were calcined at 550° C. for 4 h. Before the acetylene dimerization reaction, catalyst was reduced at 500° C. for 2 h.

Example 2: Methods for Catalyst Characterization

Transmission electron microscopy (TEM) measurements were performed on a JEOL (JEM 2100) TEM instrument operated at 200 kV accelerating voltage. X-ray diffraction (XRD) measurement was performed on a PANalytical X'Pert Pro X-ray diffraction operated under 45 kV and 40 mA with a Cu Kα radiation. An X'celerator solid-state detector with a scan speed of 5°/min was employed. The $H_2$ temperature-programmed reduction ($H_2$-TPR) was carried out to study reducibility of the catalysts using a Micromeritics Autochem 2950. The catalyst (0.1 g) was pretreated at 300° C. under argon at flow rate of 50 mL/min for 1 h and then cooled to 50° C. TPR was performed from 100 to 900° C. with a ramping rate of 10° C./min under 10% $H_2$ in argon (50 mL/min) flow. Temperature-programmed desorption of ammonia ($NH_3$-TPD) was conducted on the Micromeritics Autochem 2950. Prior to each $NH_3$-TPD run, the catalyst (0.05 g) was dried at 300° C. for 30 min under helium (50 mL/min), and then cooled to 100° C. After this procedure, the catalyst was heated again to 50° C. at a ramping rate of 10° C./min and exposed to 30 mL/min of 15% $NH_3$ in Helium for 35 min. Finally, the catalyst was purged with helium for 30 min to remove excess $NH_3$ before temperature was ramped up to 800° C. (5° C./min). The X-ray photoelectron spectroscopy (XPS) measurement was carried out using a PHI 5000 Versa Probe system (Physical Electronics) to study the valences of Cu before and after the reaction. The reference peak selected was the C 1s peak at 284.8 eV for the calibration of binding energies of all XPS spectra.

Example 3: Catalytic Activity Evaluation

The dimerization of acetylene was carried out in a fixed-bed reactor made of stainless steel. The feedstock was a gas mixture consisting of hydrogen, nitrogen (as internal standard), and acetylene and argon (5 vol % of acetylene, and argon as balance gas). In a typical experiment, 0.2 g catalyst was loaded in the reactor and reduced under hydrogen (5 mL/min) for 2 h. The catalyst was cooled to room temperature when the feedstock gas mixture was introduced at space velocity of 36000 mL/g·h. The pressure for the dimerization was controlled by a back-pressure regulator. The products were analyzed by an online GC (INFICON, Micro GC fusion) equipped with a thermal conductivity detector and Rt-Molsieve 5A, Rt-U-Bond, Alumina $Na_2SO_4$ and Rxi-1 ms columns.

The conversion of acetylene (X), the selectivity of products ($S_i$, $S_j$, $S_{benzene}$ and $S_{total}$) are calculated as followings. The selectivity to three butene isomers, t-2-butene, 1-butene, c-2-butene was combined and reported as butene.

$$X = \frac{C_2H_2 \text{ (in)} - C_2H_2 \text{ (out)}}{C_2H_2 \text{ (in)}} * 100\%;$$

$$S_i = \frac{C_i \text{ (out)}}{\sum C_i\text{(out)} + 2\sum C_j\text{(out)} + 3C_{benzene} \text{ (out)}} * 100\%;$$

-continued $$S_j = \frac{2C_j \text{ (out)}}{\sum C_i(\text{out}) + 2\sum C_j(\text{out}) + 3C_{benzene} \text{ (out)}} *100\%;$$

$$S_{benzene} = \frac{3C_{benzene} \text{ (out)}}{\sum C_i(\text{out}) + 2\sum C_j(\text{out}) + 3C_{benzene} \text{ (out)}} *100\%;$$

$$S_{total} = \sum S_h \text{ } (h = 2, 4).$$

In the above calculation, $C_2H_2$ (in) and $C_2H_2$ (out) stand for the concentration of acetylene in the feed and in the products, respectively. C stands for the concentration of the products such as acetylene, ethylene and ethane, $C_i$ stands for the concentration of the products of t-2-butene, 1-butene, c-2-butene, 1,3-butadiene; $S_{total}$ stands for the total selectivity of $C_2$ or $C_4$.

Example 4: Catalyst Characterization

Figure 1C:
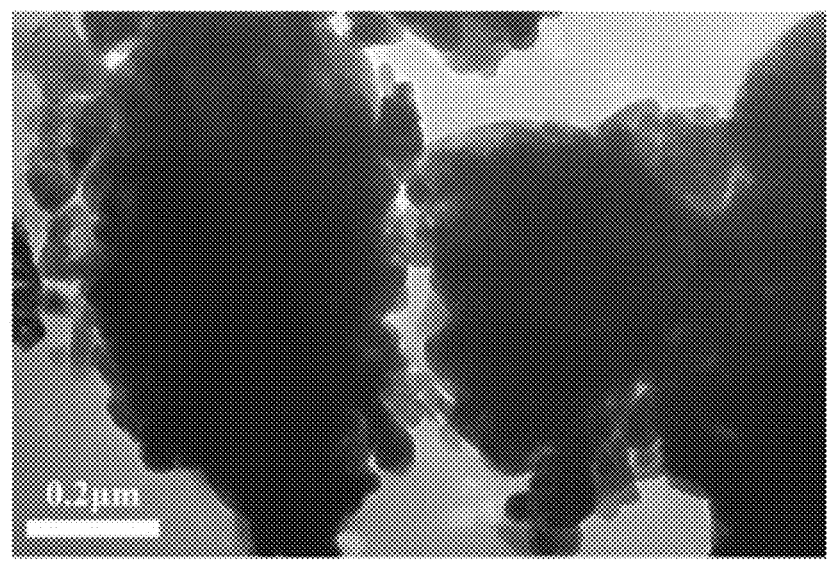
Figure 1D:
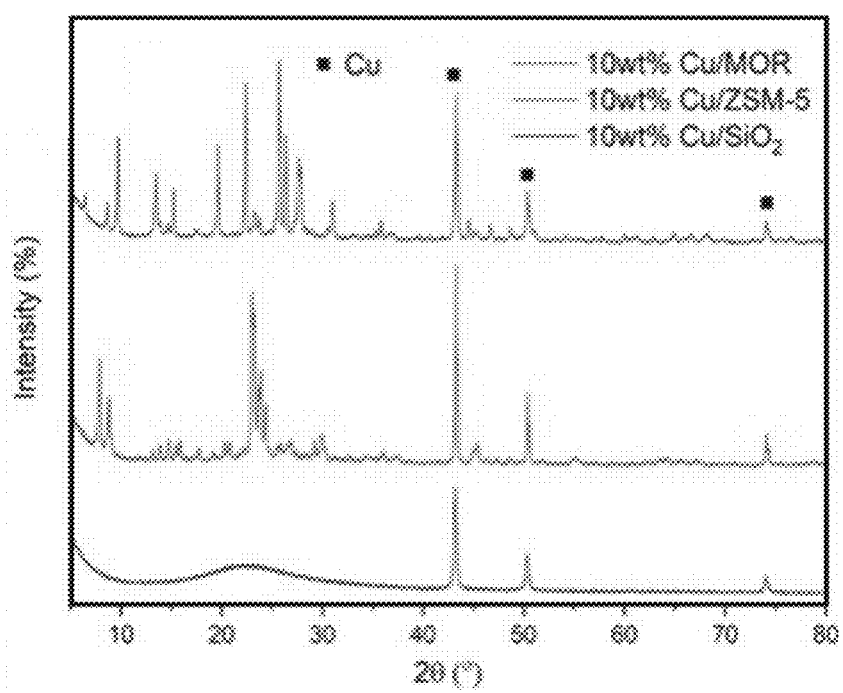
Figure 1E:
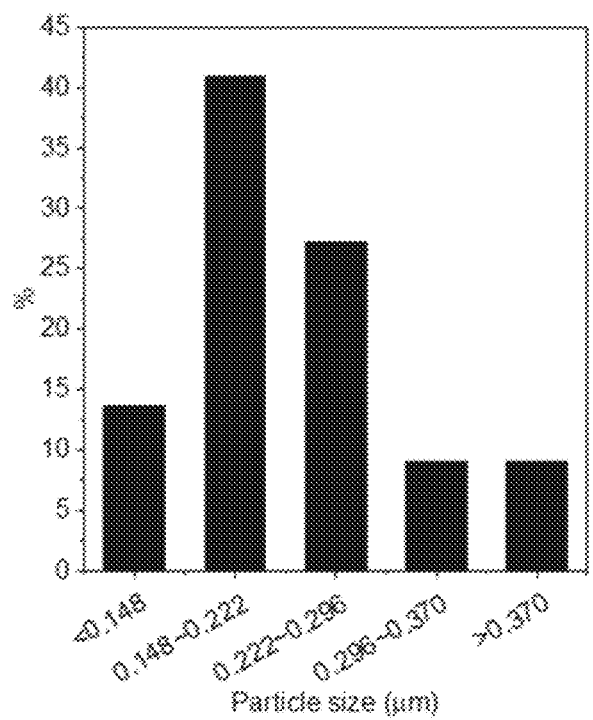
Figure 1F:
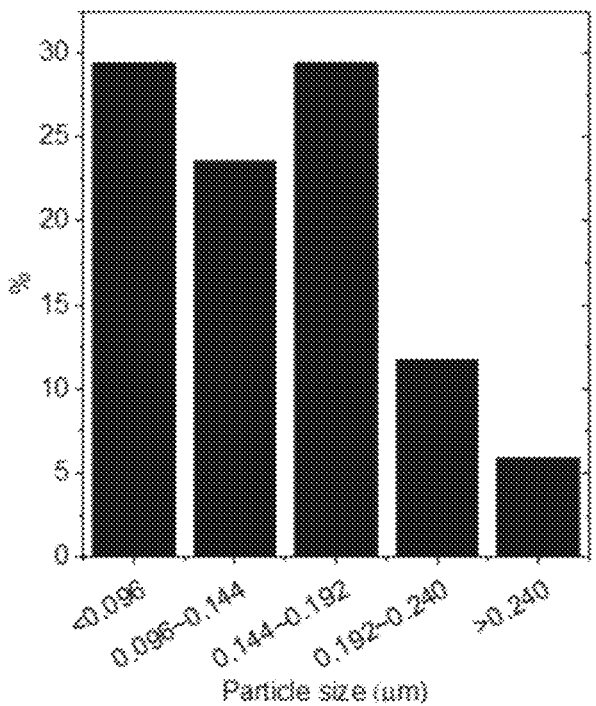
Figure 1G:
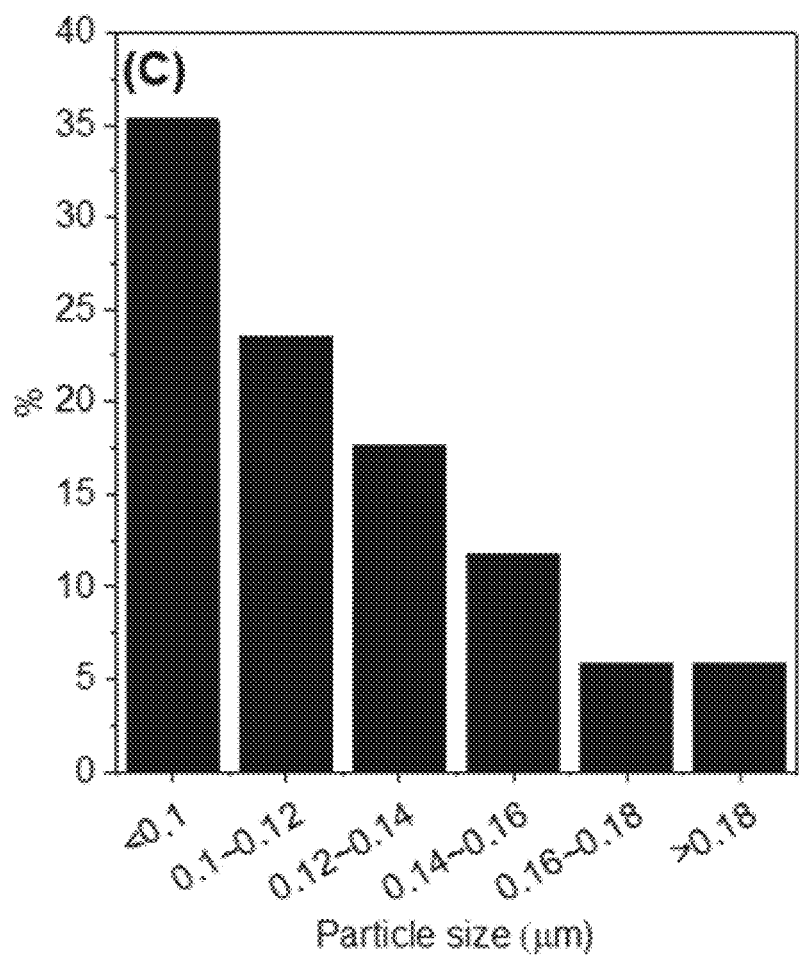

TEM images were collected, showing the morphologies of the as-prepared 10 wt % $Cu/SiO_2$ (FIG. 1A), 10 wt % Cu/ZSM-5 (FIG. 16), 10 wt % Cu/MOR (FIG. 1C) catalysts and their XRD patterns (FIG. 1D). Small metal particles were observed on the surface of ZSM-5 and MOR supports. The particle size of copper on 10 wt % Cu/ZSM-5 catalyst seemed to be smaller than that on the 10 wt % Cu/MOR catalysts. It is well known that the structure of MOR contains 12-membered ring pores (7.0×6.5 Å) and 8-membered ring channels (5.7×2.6 Å) which are interconnected by 8-membered ring side pockets in the middle. While the structure of ZMS-5 is a three dimensional 10-membered ring channel containing two type of interconnected channels: straight channels (5.6×5.3 Å) and sinusoidal channels (5.5×5.1 Å); these provide smaller channel space than the that of MOR zeolite. This may be one of reasons why copper particles on ZSM-5 appeared to be smaller than on MOR support. The diffraction peak at 22° in FIG. 1D for 10 wt % $Cu/SiO_2$ catalysts was attributed to the amorphous $SiO_2$, which was also shown the irregular shape in FIG. 1A. The diffraction peaks at 43.30°, 50.43°, and 74.13° for 10 wt % $Cu/SiO_2$, 10 wt % Cu/ZSM-5 and 10 wt % Cu/MOR catalysts in FIG. 1D were ascribed to the (111), (200) and (220) lattices of copper.

Textural properties derived from $N_2$ adsorption-desorption measurements of the as-prepared catalysts are shown in Table 1 below. Apparently, the surface area, pore volume and average pore size are very different for 10 wt % $Cu/SiO_2$, 10 wt % Cu/ZSM-5 and 10 wt % Cu/MOR catalysts. The pore volume and average pore size based on the BJH method for 10 wt % Cu/MOR catalyst are 0.10 cm³/g and 23.75 Å respectively, which are bigger than those for 10 wt % Cu/ZSM-5 catalyst (0.06 cm³/g and 23.40 Å).

Figure 2A:
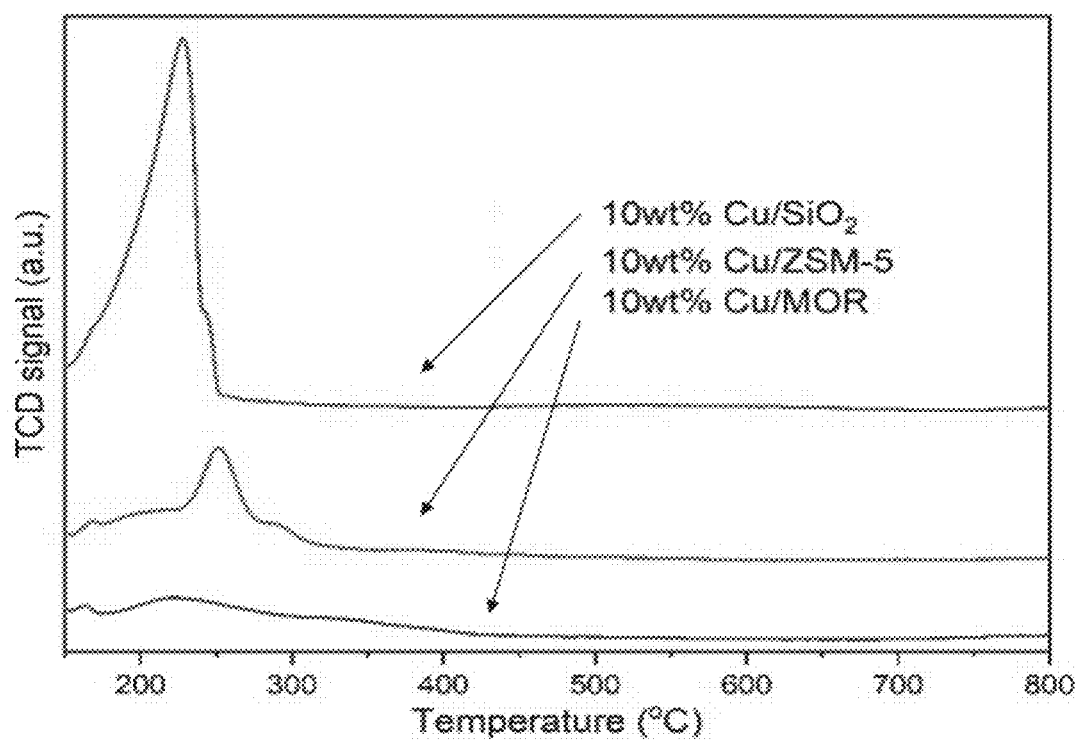
FIGS. 2A-2B show representative Hz-temperature programmed reduction (HrTPR) and $NH_3$-temperature programmed desorption ($NH_3$-TPD) data relating to disclosed catalysts.

$H_2$-temperature programmed reduction (HrTPR, FIG. 2A) and $NH_3$-temperature programmed desorption ($NH_3$-TPD, FIG. 2B) were performed using on 10 wt % $Cu/SiO_2$, 10 wt % Cu/ZSM-5 and 10 wt % Cu/MOR catalysts. All $H_2$-TPR profiles exhibit two main peaks which can be ascribed to the consumption of hydrogen. In general, the reduction of bulk Cu follows a two-step process. First, CuO is reduced to $Cu_2O$, then $Cu_2O$ is further reduced to Cu with the increase in temperature under hydrogen atmosphere. Reduction peaks located at 227, 250 and 226° C. for these three catalysts are attributed to the overlapping of reduction peaks associate with CuO and $Cu_2O$. The deviation of peak positions may be due to the interaction of copper with different supports. The peak at about 168° C. is mainly due to the reduction of highly dispersed copper oxide species or small two- and three-dimensional clusters.

Figure 2B:
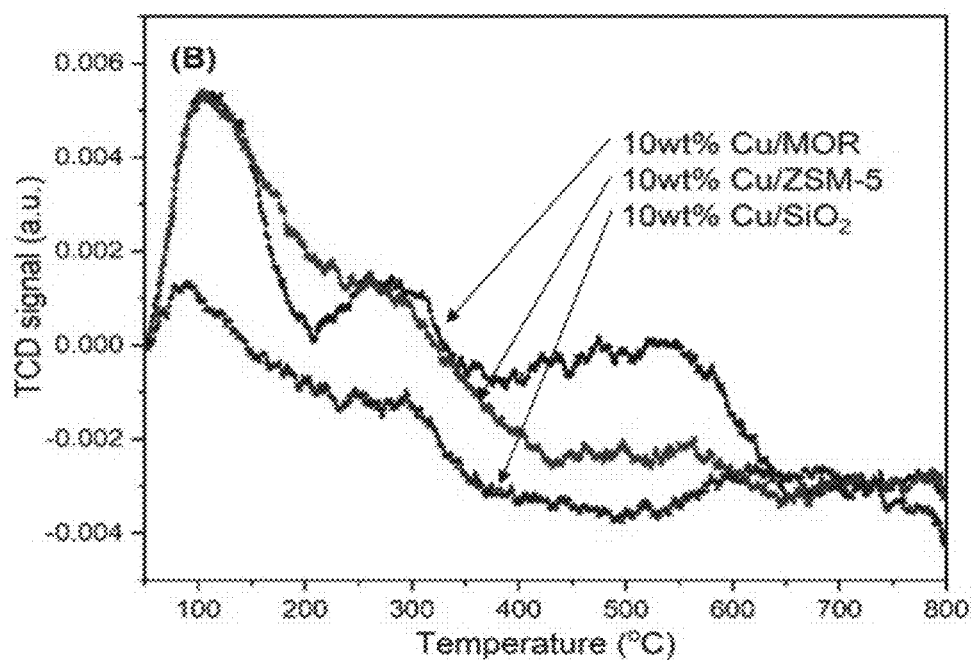

Acid site distribution and strength measured by $NH_3$-TPD are shown in FIG. 2B. All of three catalysts shows three desorption peaks within a temperature range of 50-800° C. The peak centered at about 122° C. is assigned to the desorption of $NH_3$ which is weakly absorbed on weak strength acid sites. The peak around 272° C. is ascribed to the desorption of $NH_3$ which is adsorbed on the medium strength acid sites, and the peak around 529° C. (or 680° C. for 10 wt % $Cu/SiO_2$ catalyst) can be ascribed to the desorption of $NH_3$ which is adsorbed on the strong acid sites. Furthermore, the proportion of acid sites corresponding to each peak was calculated according to its peak area in the total areas. The total (weak acid+medium acid) sites for 10 wt % $Cu/SiO_2$, 10 wt % Cu/ZSM-5 and 10 wt % Cu/MOR catalysts are 44.5%, 74.3% and 79.8%, respectively.

Example 5: Effect of Support on the Hydrodimerization of Acetylene

Figure 3A:
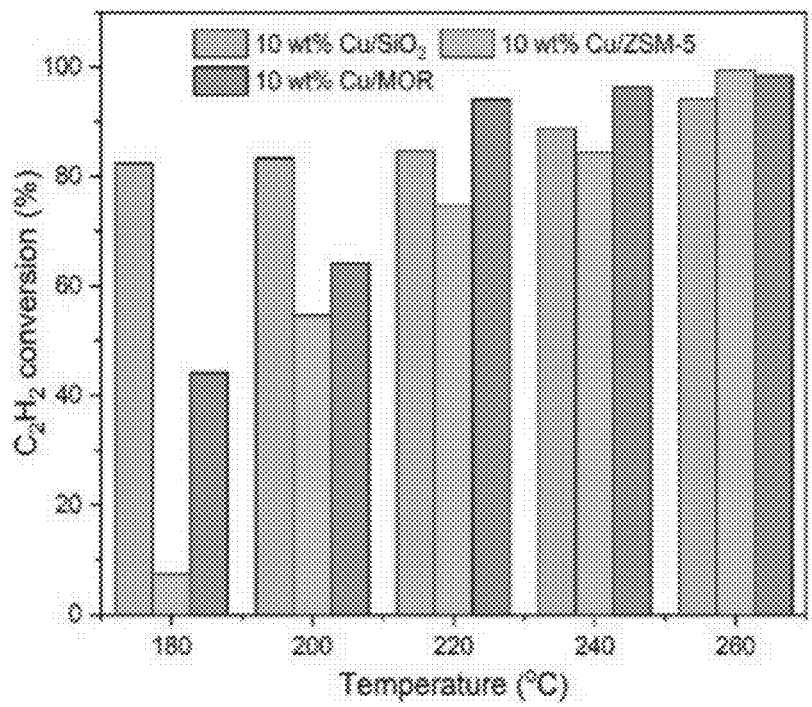
FIGS. 3A-3D shows representative data relating to the effect of temperature on acetylene conversion and selectivity over different supported copper catalysts.
Figure 3B:
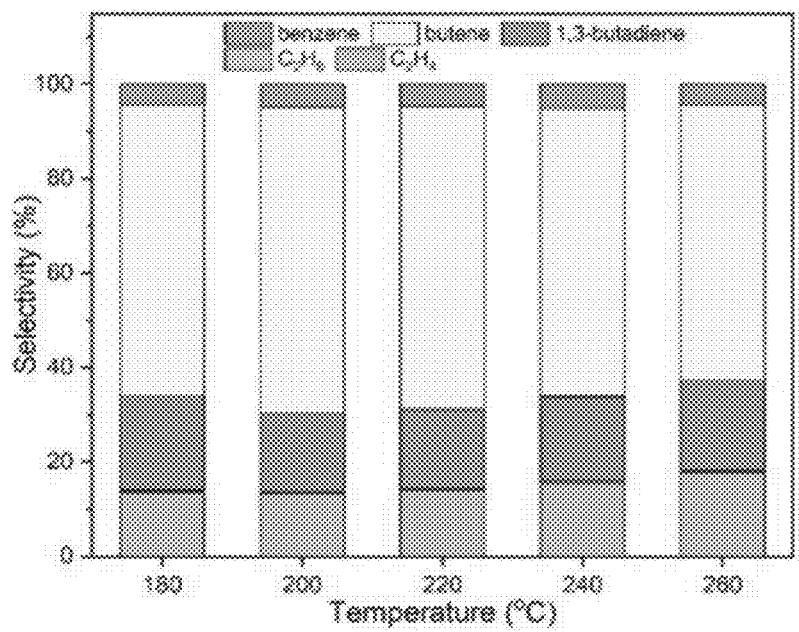

The conversion and selectivity from hydrodimerization of acetylene were evaluated over three catalysts. The products consist of $C_2$ (ethylene and ethane), $C_4$ (t-2-butene, 1-butene, c-2-butene, and 1,3-butadiene), and benzene. Hereafter, $C_4$ refers to butene and 1,3-butadiene. As illustrated in FIG. 3, for all three catalysts, the conversion of acetylene increases with the increasing in reaction temperature. Very small amounts of undesired product ethane is observed and no butane is produced, indicating over-hydrogenation reactions are inhibited. The selectivity to $C_2$, $C_4$ olefins and benzene appears to be different. As shown in FIG. 3A, over the 10 wt % $Cu/SiO_2$ catalyst, the acetylene conversion is higher at relatively low temperature than the other two catalysts, and the selectivity to $C_4$ olefins (butene and 1,3-butadiene) is slightly decreased from 82% to 77% in the range of 180 to 260° C. (FIG. 3B). Although the selectivity to $C_4$ olefins decreases with the temperature, the selectivity to 1,3-butadiene reached the lowest point at 200°

TABLE 1

Textural Properties of Cu-based Catalysts

| Catalyst | BET Surface Area (m²/g) | Pore Volume (cm³/g) | Average Pore Size (Å) |
|---|---|---|---|
| 10 wt % Cu/MOR | 361 | 0.10 | 23.75 |
| 10 wt % Cu/ZSM-5 | 275 | 0.06 | 23.40 |
| 10 wt % Cu/SiO₂ | 246 | 1.15 | 18.18 |
| 1 wt % Ru10 wt % Cu/MOR | 322 | 0.11 | 23.99 |
| 1 wt % Ga10 wt % Cu/MOR | 336 | 0.10 | 24.68 |
| 1 wt % Ag10 wt % Cu/MOR | 353 | 0.13 | 25.11 |
| 1 wt % Pd10 wt % Cu/MOR | 345 | 0.12 | 24.71 |

Figure 3C:
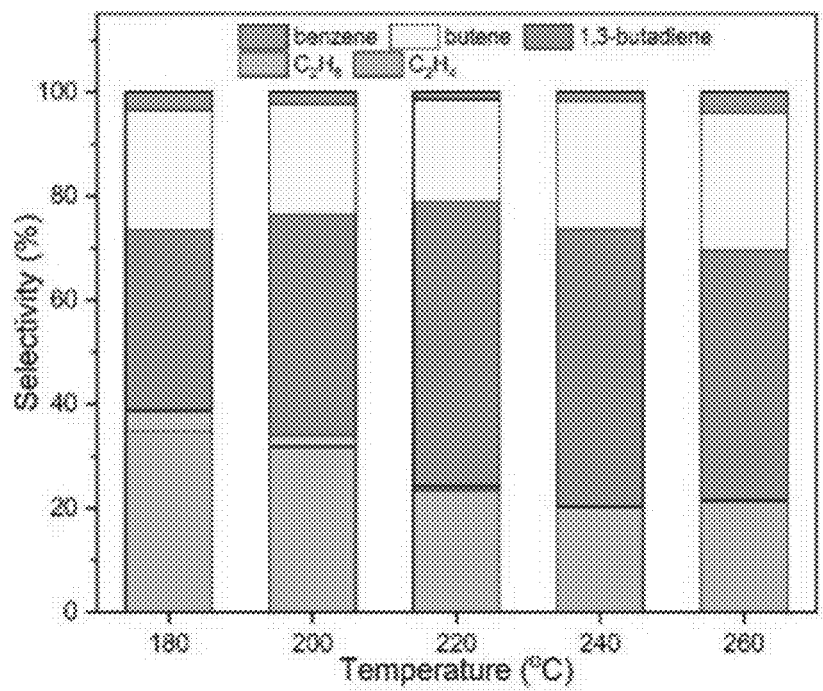
Figure 3D:
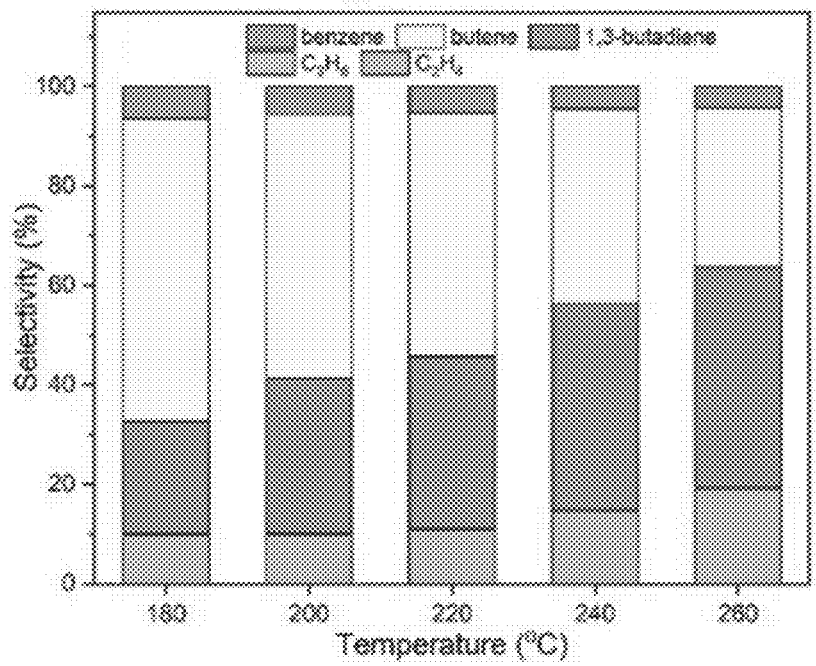

C. (around 17%); Meanwhile the selectivity to butene reached the highest point at 200° C. (around 65%). It seems like the selectivity to 1,3-butadiene and butene exhibits the opposite trend during the reaction. This opposite trend may be due to the further hydrogenation of 1,3-butadiene to butene in the reaction process. As shown in FIG. 3C, over 10 wt % Cu/ZSM-5 catalyst, the selectivity to $C_4$ olefins is increased with temperature and reaches the highest point at 240° C. Among the different $C_4$ olefins, the selectivity to 1,3-butadiene is dominant in the products and even reaches 55% at 220° C. The selectivity to $C_4$ olefins over 10 wt % Cu/MOR catalyst shows the same trend as 10 wt % Cu/ZSM-5 catalyst, and reaches the highest point of 84% at 220° C. (FIG. 3D). In contrast, at 220° C., the selectivity to $C_4$ olefins is only 74% over 10 wt % Cu/ZSM-5 catalyst (FIG. 3C). Though the selectivity to 1,3-butadiene over 10 wt % Cu/ZSM-5 catalyst is higher than that over 10 wt % Cu/MOR catalyst at 220° C., the conversion of acetylene over 10 wt % Cu/MOR catalyst is much higher than that over 10 wt % Cu/ZSM-5 catalyst. The following experiments were carried out at 220° C. to determine the effects of process conditions (molar ratio and pressure). In addition, the selectivity for 1,3-butadiene is increased in the range of 160 to 280° C., while the selectivity for butene is reduced at the same time, indicating the higher temperature is beneficial to the selectivity to 1,3-butadiene. As previously reported, Cu-based catalysts could react with acetylene to form a π- and/or a σ-complex, the surface intermediate rapidly dimerize to form $C_4$ olefins. Interestingly, over conventional Nieuwland catalyst, monovinylacetylene (MVA) can be obtained immediately after the $C_4$ intermediates are formed in the liquid media. It appears that the catalytic behavior and reaction pathways are different in gas-solid reaction systems because the products consist of t-2-butene, 1-butene, c-2-butene and 1,3-butadiene without forming MVA (Scheme 1).

reported, two acetylene molecules were adsorbed and activated on the surface of catalyst to form $C_4H_4$ intermediate via a dimerization reaction. Subsequently, another acetylene molecular was added to form the benzene molecule (Scheme 3). Furthermore, higher pressure favors the recombination of $C_4H_4$ and acetylene to form a metallocyclic intermediate which can disrupt the adsorption of acetylene to form benzene. As shown in FIGS. 3B-D, the selectivity for benzene over 10 wt % Cu/$SiO_2$, 10 wt % Cu/MOR and 10 wt % Cu/ZSM-5 catalysts is not sensitive to the temperature. This is probably because the intermediate for benzene formation via acetylene trimerization is more difficult to develop as compare to the formation of intermediate for acetylene dimerization.

Scheme 3

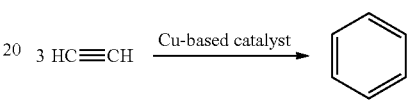

FIG. 4 shows the TEM images and XRD patterns for 1 wt % Ru 10 wt % Cu/MOR, 1 wt % Ga 10 wt % Cu/MOR, 1 wt % Ag 10 wt % Cu/MOR, and 1 wt % Pd 10 wt % Cu/MOR catalysts. Compared with TEM image of 10 wt % Cu/MOR catalyst shown in FIG. 1C, in addition to copper particle observed on the surface of the MOR support, the promoter metal particles of Ru, Ag and Pd can be observed in FIGS. 4A, 4C, and 4D, respectively. The diameters of these promoter metal particles are different, with the smallest being Pd particles which are dispersed on the surface of the MOR support. Interestingly, the core-shell structured particles are observed in FIG. 4B. This is probably because Ga is coated on the surface of copper after the reduction at 500° C.

Scheme 1

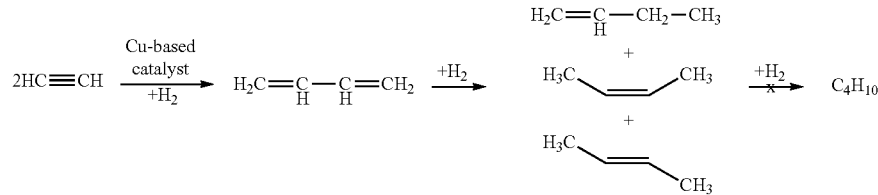

Generally, the dissociated hydrogen and acetylene can also form a vinyl intermediate on the surface of catalyst under the reaction conditions. The vinyl intermediate could accept protons to from ethylene and ethane (Scheme 2). As shown in FIGS. 3B-D, the selectivity for $C_2$ products that consist of mainly ethylene increases slowly with the increase in temperature over 10 wt % Cu/$SiO_2$ and 10 wt % Cu/MOR catalysts, while it decreases gradually with the increase in temperature over 10 wt % Cu/ZSM-5 catalyst.

Scheme 2

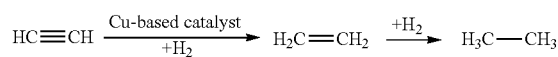

Figure 4A:
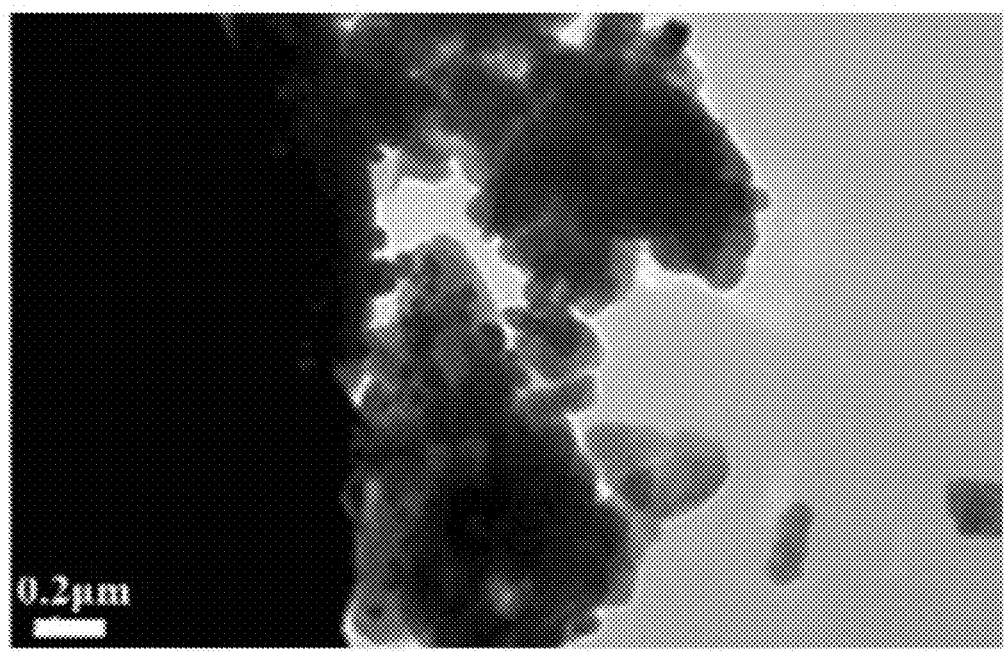
FIG. 4A-4E shows representative data as follows.
Figure 4B:
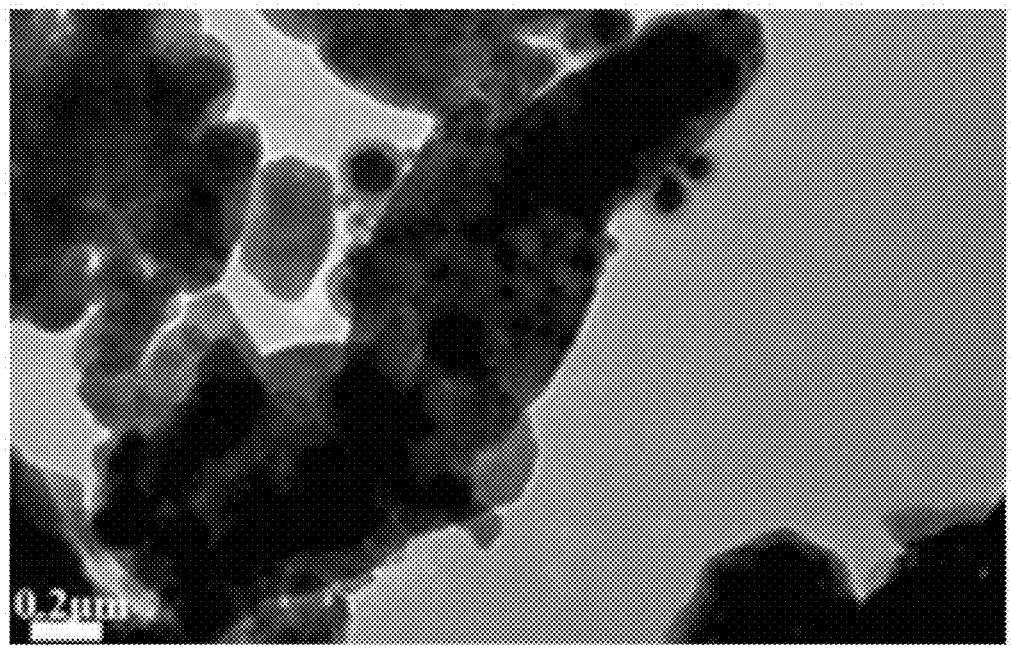
Figure 4C:
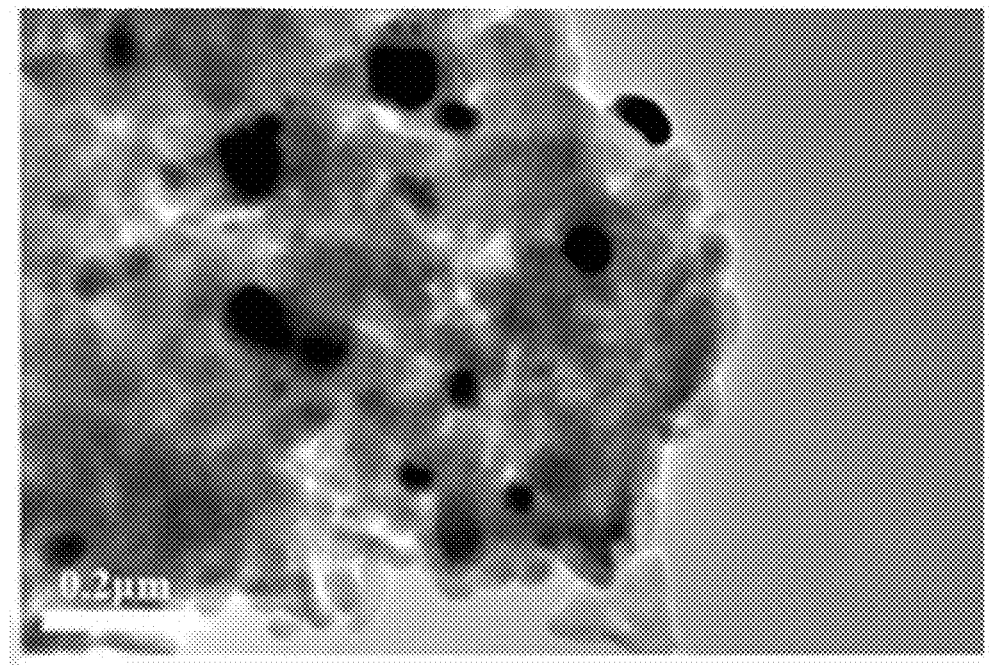
Figure 4D:
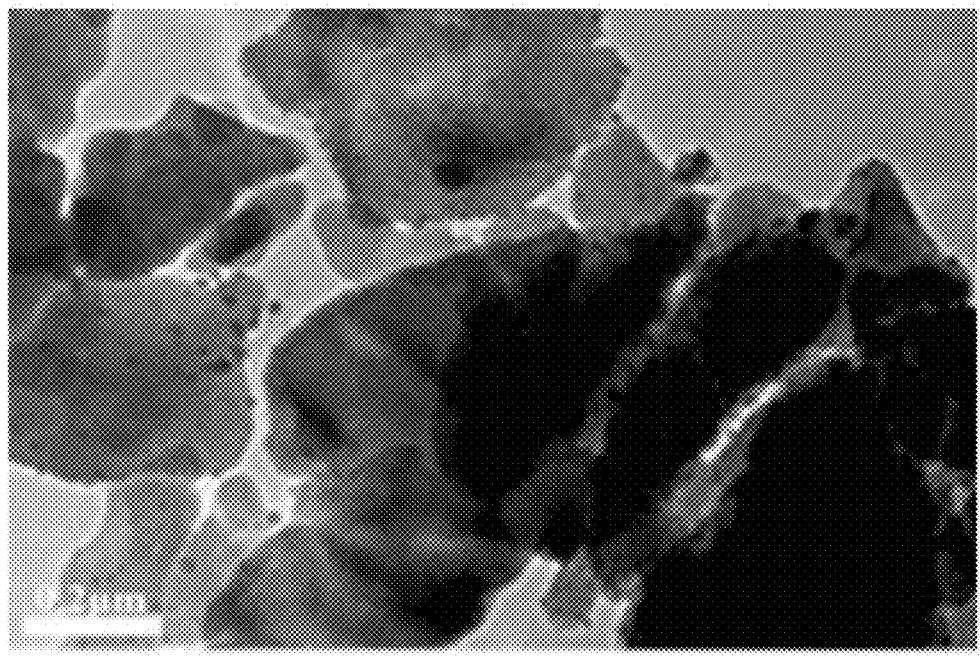
Figure 4E:
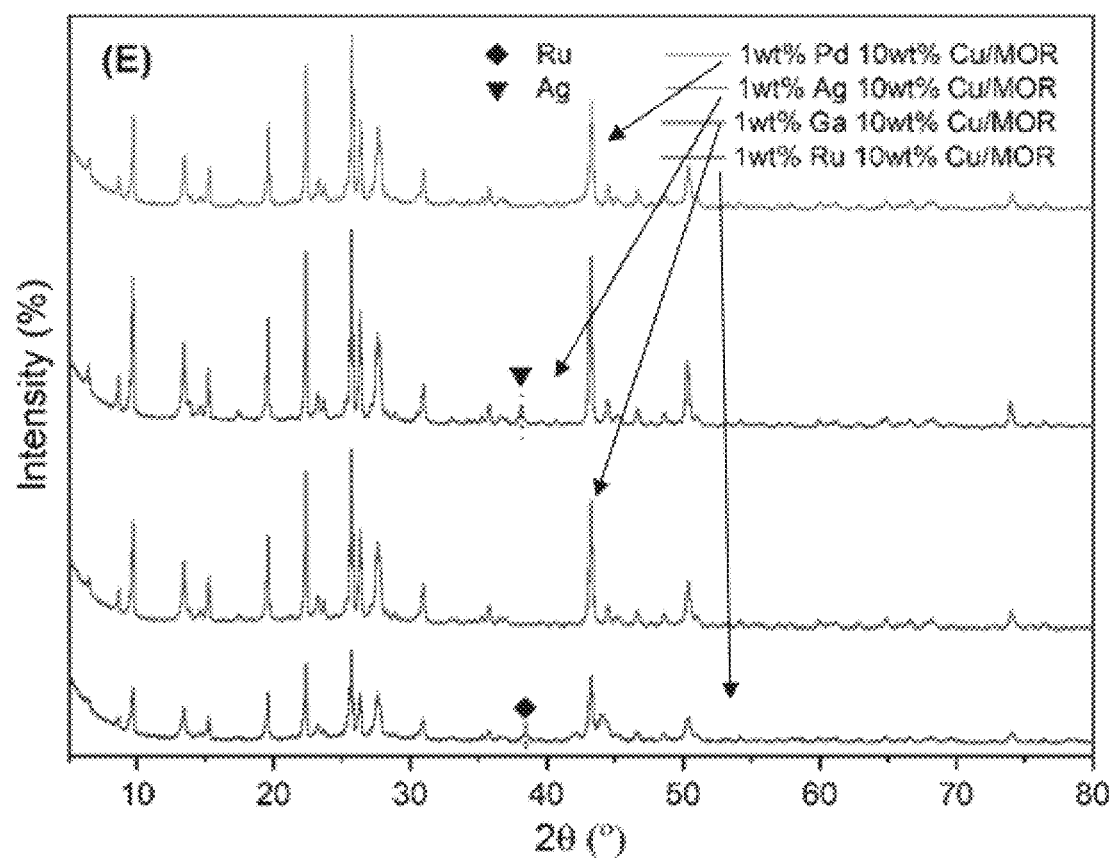

Additionally, a small amount of benzene was observed in the products over all the three catalysts. As previously Moreover, when Ga is coated on the surface of copper, it blocks the interaction between acetylene and copper in acetylene hydrodimerization reaction, leading to much lower acetylene conversion as compared with 10 wt % Cu/MOR catalyst. The XRD patterns for the catalysts are exhibited in FIG. 4E. The diffraction peaks of copper and MOR are shown in the XRD spectra. Specifically, in FIG. 4E, the diffraction peaks located at 38.4° and 38.0° are ascribed to promoter metals Ru and Ag, respectively. It is difficult to observe the diffraction peaks for either Pd or Ga. This is probably due to the low concentration of metals or high dispersion of Pd on the surface of MOR (FIG. 4D).

Figure 5B:
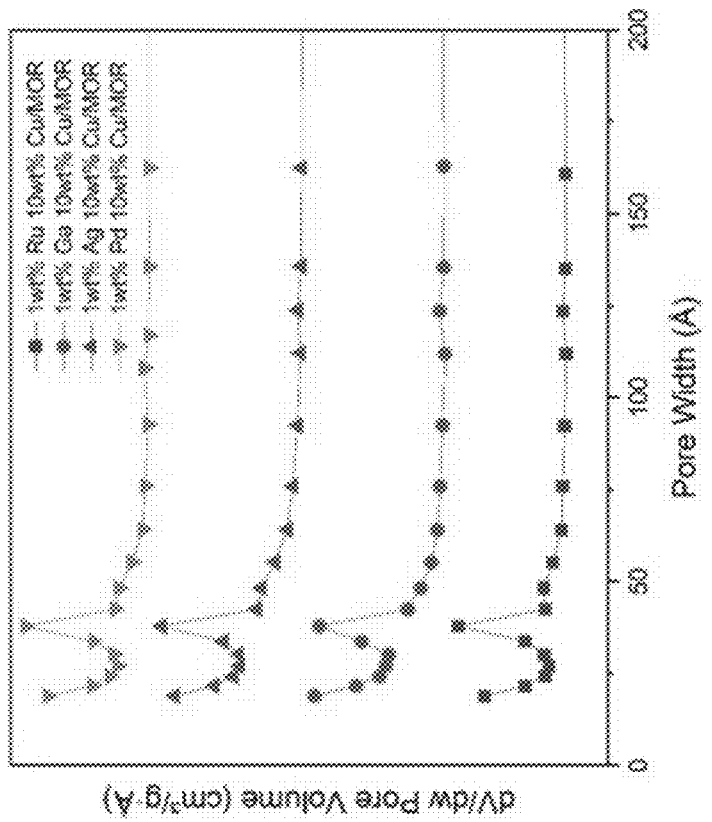
FIG. 5B pore size distributions.
Figure 5A:
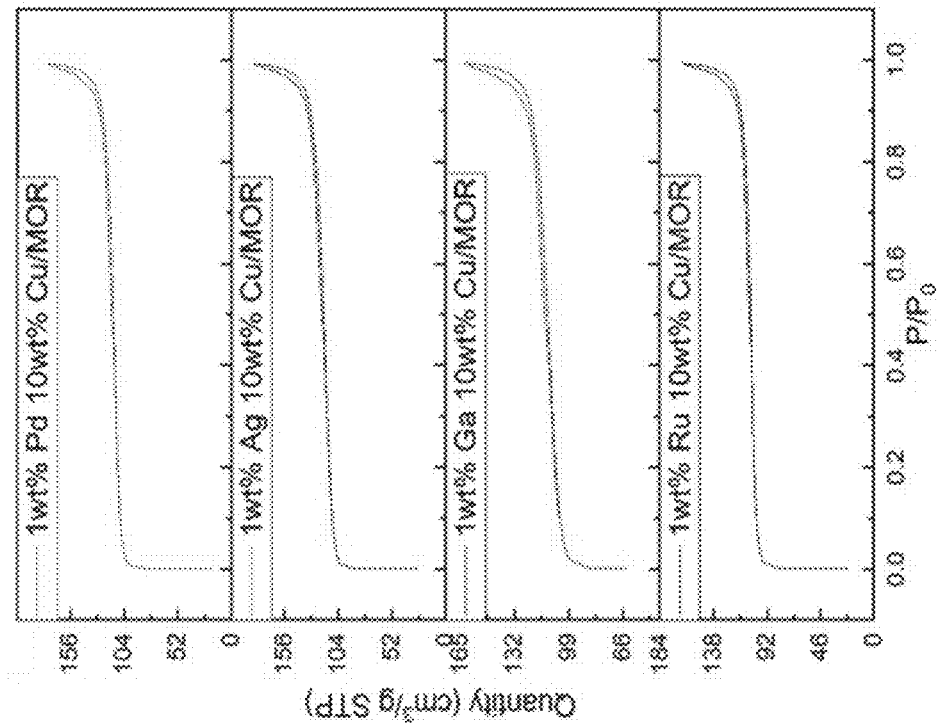
FIG. 5A $N_2$ adsorption-desorption isotherms.

FIG. 5 shows the nitrogen adsorption-desorption isotherms (A) and pore size distributions (B) for 1 wt % Ru 10 wt % Cu/MOR, 1 wt % Ga 10 wt % Cu/MOR, 1 wt % Ag 10 wt % Cu/MOR and 1 wt % Pd 10 wt % Cu/MOR catalysts. According to IUPAC classification, all isotherms shown in FIG. 5A are ascribed to a type I curve, which is the typical characteristic of microporous materials. The BET surface area, the pore volume and the average pore size were listed in Table 1. It can be seen that the BET surface areas of all four metal-promoted 10 wt % Cu/MOR catalysts are smaller than unpromoted 10 wt % Cu/MOR catalyst, which is attributed to the covering of the channel surface by these promoters (Ru, Pd, Ag, Ga). Although the surface areas of above four catalysts are different, their pore widths are almost the same (37.8 Å, FIG. 5B).

Figure 6A:
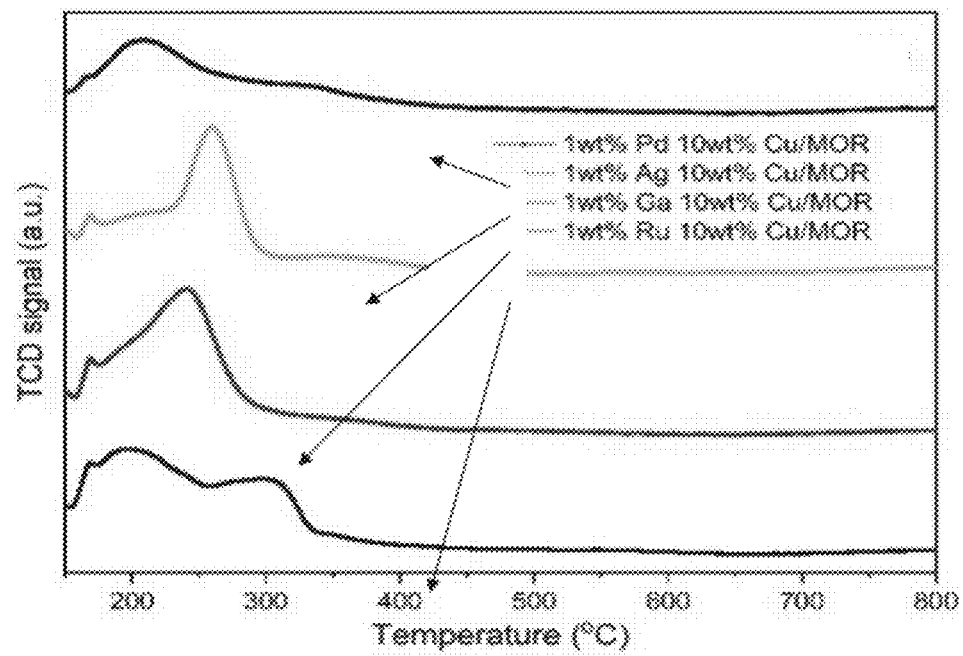
FIG. 6 shows HrTPR measurement (FIG. 6A) and $NH_3$-TPD (FIG. 6B) for Cu-based catalysts.
Figure 6B:
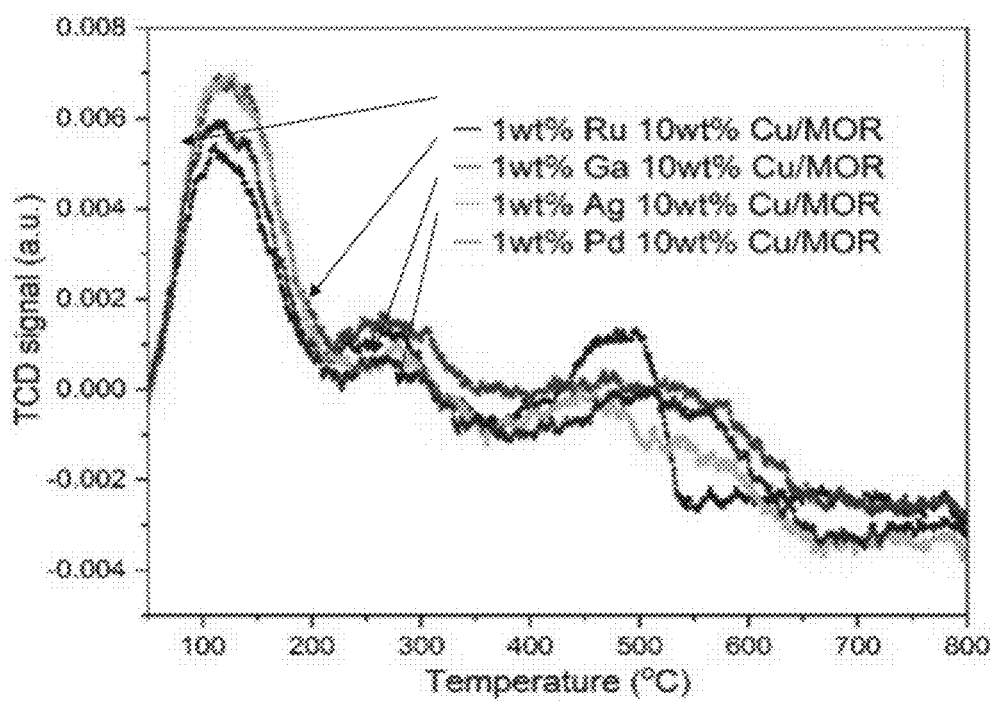

FIG. 6 shows $H_2$-TPR and $NH_3$-TPD profiles based on 1 wt % Ru 10 wt % Cu/MOR, 1 wt % Ga 10 wt % Cu/MOR, 1 wt % Ag 10 wt % Cu/MOR and 1 wt % Pd 10 wt % Cu/MOR catalysts. All four catalysts exhibit an identical small peak at about 168° C. (FIG. 6A), which is mainly due to the reduction of highly dispersed copper oxide species or small two- and three-dimensional clusters. For 1 wt % Ru 10 wt % Cu/MOR catalyst, the peak at 301° C. is ascribed to the reduction of $RuO_x$ to $Ru^0$ species that strongly interact with the support. The peak at 196° C. is attributed to the reduction of bulk CuO, which is lower than that over 10 wt % Cu/MOR catalyst located at about 226° C. The addition of Ru promotes the reduction of Cu, shifting TPR peak to lower temperature. The peak at 239° C. for 1 wt % Ga 10 wt % Cu/MOR catalyst is attributed to the reduction of bulk CuO, which seems to be a little higher than the reduction peak for 10 wt % Cu/MOR catalyst. This is probably because Ga species form a shell on the surface of copper (FIG. 4B), inhibiting the interaction of hydrogen with copper oxide. Moreover, it was reported that the strong interaction between active component and $Ga_2O_3$ promoter could increase the reduction temperature of active component, which could also lead to the high dispersion of the active component. For 1 wt % Ag 10 wt % Cu/MOR catalyst, the reduction peak at 259° C. is ascribed to the reduction of bulk CuO, whereas the low and broad peak around 350° C. is attributed to the reduction of $Ag_2O$ clusters on the MOR. With regard to the 1 wt % Pd 10 wt % Cu/MOR catalyst, the peak at 205° C. is attributed to the reduction of bulk CuO. The reduction peak is shifted to lower temperature compared to that over 10 wt % Cu/MOR catalyst, which is located at about 226° C. This indicates that the presence of palladium could increase the reducibility of copper on this catalyst. The results are in good agreement with a literature report. The $NH_3$-TPD profiles of these four catalysts are shown in FIG. 6B. The peaks located at around 122, 272 and 529° C. are ascribed to weak acid, medium acid, and strong acid sites which are similar to the $NH_3$-TPD profile of 10 wt % Cu/MOR catalyst shown in FIG. 26. However, the proportion of the total weak and medium acid sites increases after adding Ru, Ga, Ag and Pd promoters. As shown in FIG. 6B, the proportion of total weak acid and medium acid sites are calculated to be about 93.8%, 91.7% and 84.5% for 1 wt % Ga 10 wt % Cu/MOR, 1 wt % Ag 10 wt % Cu/MOR and 1 wt % Pd 10 wt % Cu/MOR catalysts, respectively. The proportion of total weak and medium acid sites over 10 wt % Cu/MOR catalyst is 79.8%. Interestingly, the proportion of total weak and medium acid sites over 1 wt % Ru 10 wt % Cu/MOR catalyst is just 66.7%.

Example 6: Effect of Promoters on the Hydrodimerization Reaction

FIG. 7 shows the hydrodimerization of acetylene to $C_2$, $C_4$ and benzene over 1 wt % Ru 10 wt % Cu/MOR, 1 wt % Ga 10 wt % Cu/MOR, 1 wt % Ag 10 wt % Cu/MOR and 1 wt % Pd 10 wt % Cu/MOR catalysts. It can be seen from FIGS. 7A-D that, in the presence of different promoters (Ru, Ga, Ag and Pd), the conversion of acetylene and the selectivity for $C_2$, $C_4$ and benzene are very different over the 10 wt % Cu/MOR catalyst. For Ru-promoted 10 wt % Cu/MOR catalyst, the conversion of acetylene reaches nearly 100% with the increase in reaction temperature to 200° C. (FIG. 7A). The reaction rate is significantly higher than that over 10 wt % Cu/MOR catalyst shown in FIG. 3D. The addition of Ru decreases the activation energy required for the acetylene hydrodimerization reaction. As for the selectivity for $C_4$ olefins, though a trend of declining from about 92% to 77% in the range of 180 to 260° C. is observable, selectivity is still higher than that over 10 wt % Cu/MOR catalyst. These results indicate the addition of Ru on 10 wt % Cu/MOR catalyst not only accelerates the reaction rate, but also increases the $C_4$ olefins selectivity. It is worth noting that the selectivity for 1,3-butadiene can reach 75% at 180° C. and then sharply decreases to 5% at 220° C. Meanwhile the selectivity to butene increases from 17% to 79% in the temperature range of 180 to 220° C. Moreover, the total selectivity to $C_2$ products increased from 7% to 13% in the temperature range of 180 to 260° C., which is slightly lower than the unpromoted 10 wt % Cu/MOR catalyst. In addition, compared with the total selectivity to $C_2$ (11%) and $C_4$ (84%) over 10 wt % Cu/MOR catalyst at 220° C., after addition of Ru, the total selectivity to $C_2$ and $C_4$ products already reach 9% and 87% at 200° C., respectively, indicating the addition of Ru can also improve the $C_4$ selectivity. Besides, the selectivity for benzene is also increased with the increase in temperature and reaches nearly 10% at 260° C., indicating the improved reaction rate also enhanced the contact of three activated acetylene molecular and lead to the enhanced trimerization reaction.

Figure 7A:
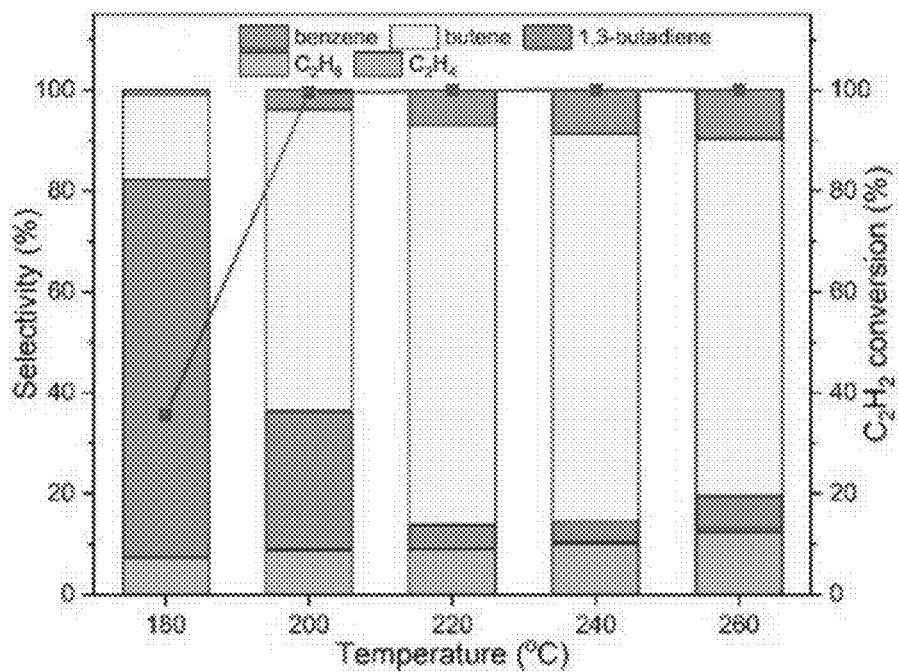
FIGS. 7A-7D shows representative data relating to the effect of temperature on product selectivity over promoted Cu-based catalysts.
Figure 7B:
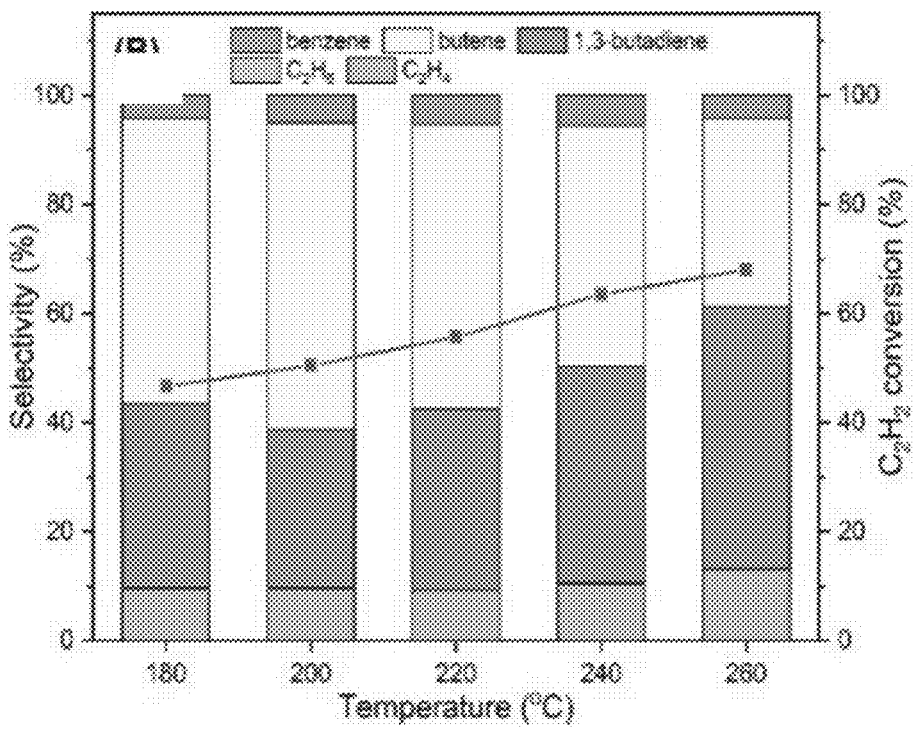

FIG. 7B shows that the addition of Ga results in lower acetylene conversion as compared with unpromoted 10 wt % Cu/MOR catalyst, even though the conversion of acetylene still increases with the increase in temperature. It is possible that the presence of Ga can isolate active sites of Ni and Pd in the catalysts. This phenomenon affects adsorption bonding energy of unsaturated hydrocarbons on the catalyst surface leading to lower reaction rate. That could be reason that causes low acetylene conversion. Moreover, FIG. 4B shows Ga is coated on the surface of Cu, preventing acetylene and hydrogen from access to the active sites, leading to lower conversion of acetylene. In the presence of Ga promoter, the selectivity to $C_4$ olefins is decreased from 86% to 83% in the temperature range of 180 to 260° C., but it is still slightly higher than the unpromoted 10 wt % Cu/MOR catalyst. Additionally, the selectivity for $C_2$ products over Ga-promoted 10 wt % Cu/MOR catalyst remains at the same level as compared with Ru-promoted 10 wt % Cu/MOR catalyst.

Figure 7C:
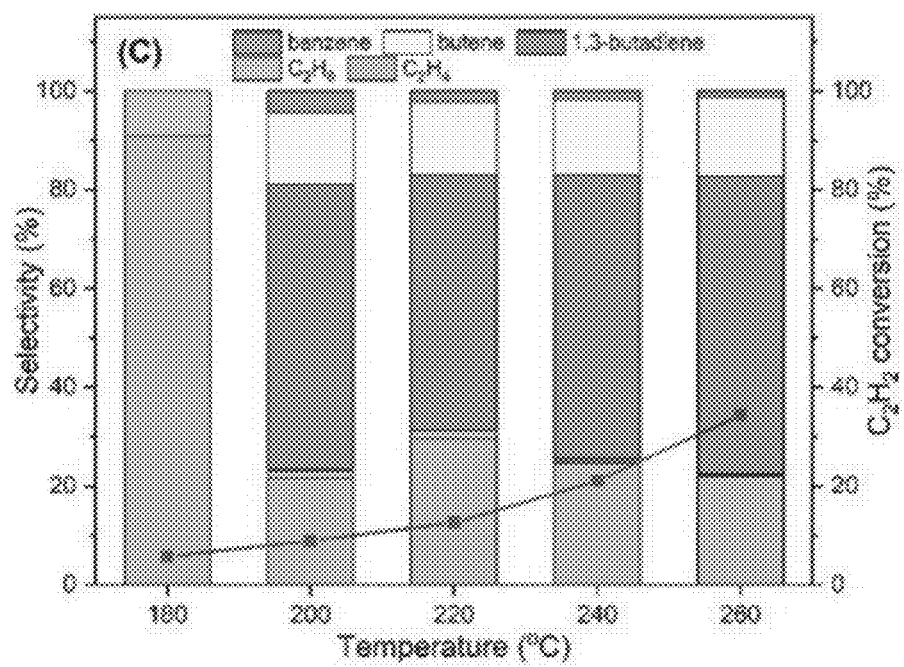

As shown in FIG. 7C, the addition of Ag into the 10 wt % Cu/MOR catalyst significantly reduces acetylene conversion. The inhibiting effect is more dramatic than adding Ga to 10 wt % Cu/MOR catalyst. This is mainly due to the inactivity of Ag to the acetylene hydroisomerization reaction and the inhibition of active component by Ag on the catalyst surface. The selectivities to $C_2$ and $C_4$ were 31% and 67% at 220° C., respectively.

Figure 7D:
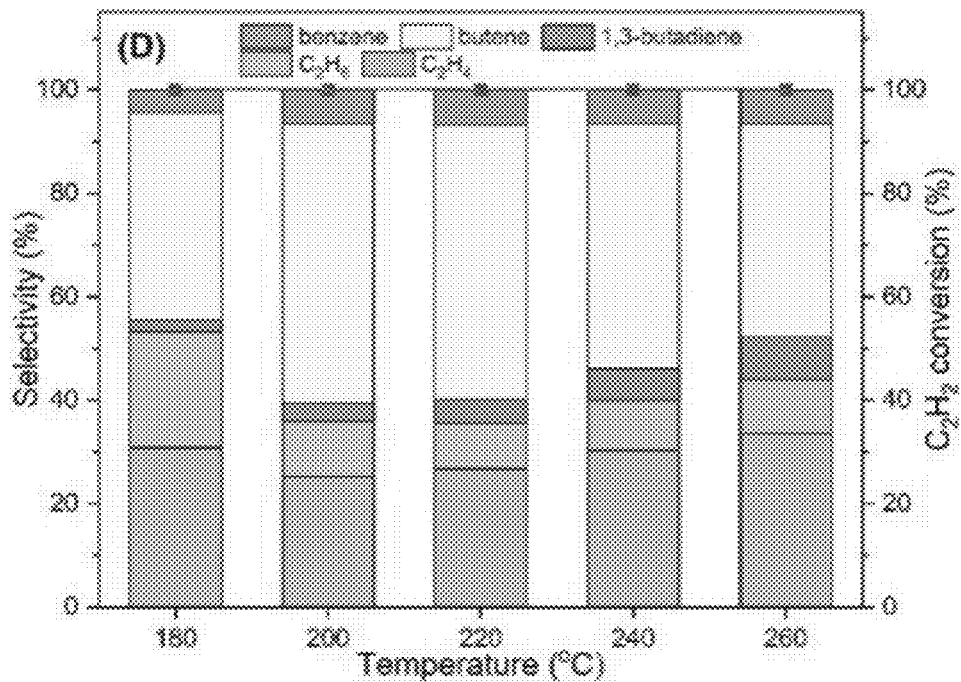

The effect of Pd promotion is shown in FIG. 7D. The addition of Pd into 10 wt % Cu/MOR catalyst significantly increases acetylene hydrodimerization activity. Even at 180° C., the conversion of acetylene already reaches 100%. Furthermore, the total selectivity for $C_2$ products is higher than that over 10 wt % Cu/MOR catalyst, almost reaching 36% at 220° C. The promotion function of Pd in selective hydrogenation was already reported. In addition, the selectivity for ethylene over 1 wt % Pd 10 wt % Cu/MOR catalyst (about 27%) at 220° C. is much higher than other catalysts which is in agreement with literature reports on selective acetylene hydrogenation to ethylene.

Example 7: Optimization of Reaction Conditions

Figure 8A:
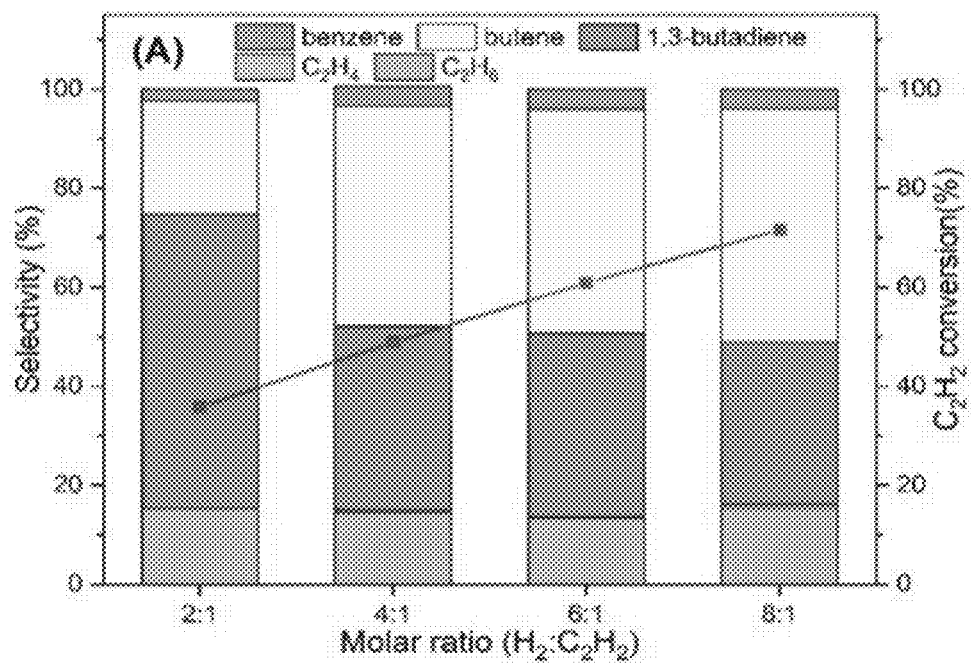
FIGS. 8A-8B shows effect of $H_2/C_2H_2$ ratio and pressure on acetylene hydrodimerization over 10% Cu/MOR catalyst.

The effects of molar ratio of hydrogen to acetylene and the reaction pressure on hydrodimerization of acetylene were studied. Although the conversion of acetylene is increased with the increase in $H_2/C_2H_2$ molar ratio under ambient pressure at 220° C. (FIG. 8A), the selectivity for $C_4$ olefins remains at the same level of about 80-82%. It is worth noting that the selectivity for 1,3-butadiene is decreased from 59% to 33% with the increase in $H_2$:$C_2H_2$ molar ratio from 2:1 to 8:1; meanwhile the selectivity to butene is increased under the same conditions. This indicates higher hydrogen partial pressure favors the formation of butene obviously converted from 1,3-butadiene. The selectivity for $C_2$ is less sensitive to the increase in $H_2/C_2H_2$ ratio as compared with $C_4$ olefins selectivity, which remains at around 15% during the process.

Figure 8B:
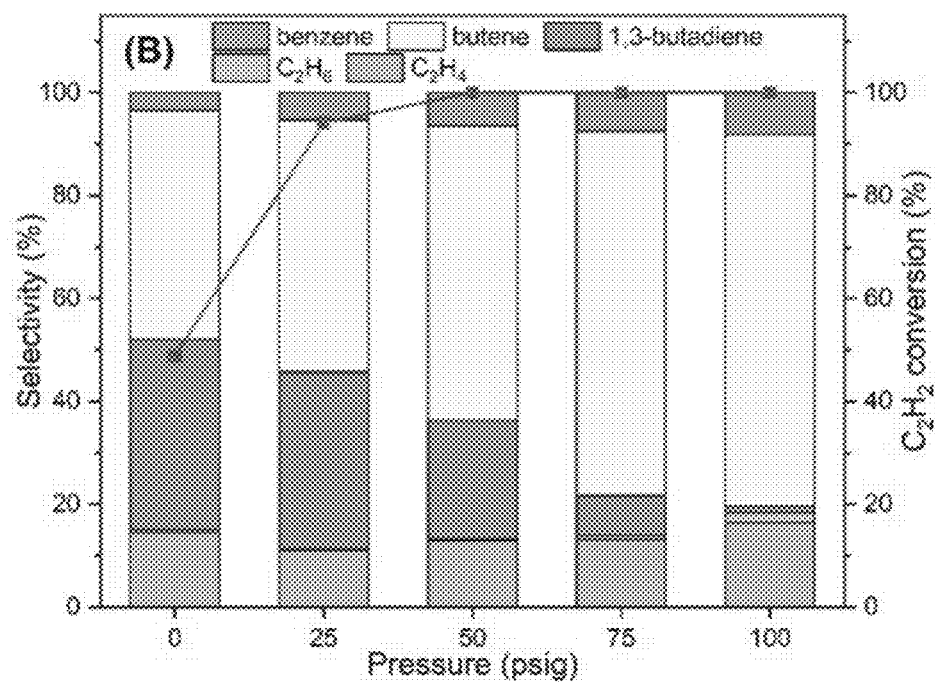

The effect of reaction pressures on the acetylene hydrodimerization is shown in FIG. 8B. The increase in reaction pressure apparently has positive effect on the conversion of acetylene, which reaches 100% at 50 psig. The selectivity for $C_4$ products reaches the highest level of about 84% under 25 psig, though the selectivity for 1,3-butadiene is decreased in the range of 0 to 100 psig. On the contrary, the selectivity for butene is increased due to the hydrogenation of 1,3-butadiene. High pressure favors the formation of benzene due to the combination of $C_4H_4$ intermediate and acetylene. Hence, the selectivity to benzene increases from 3% to 8% in the pressure range of 0 to 100 psig (FIG. 8B).

Example 8: Reaction Pathways

Figure 9:
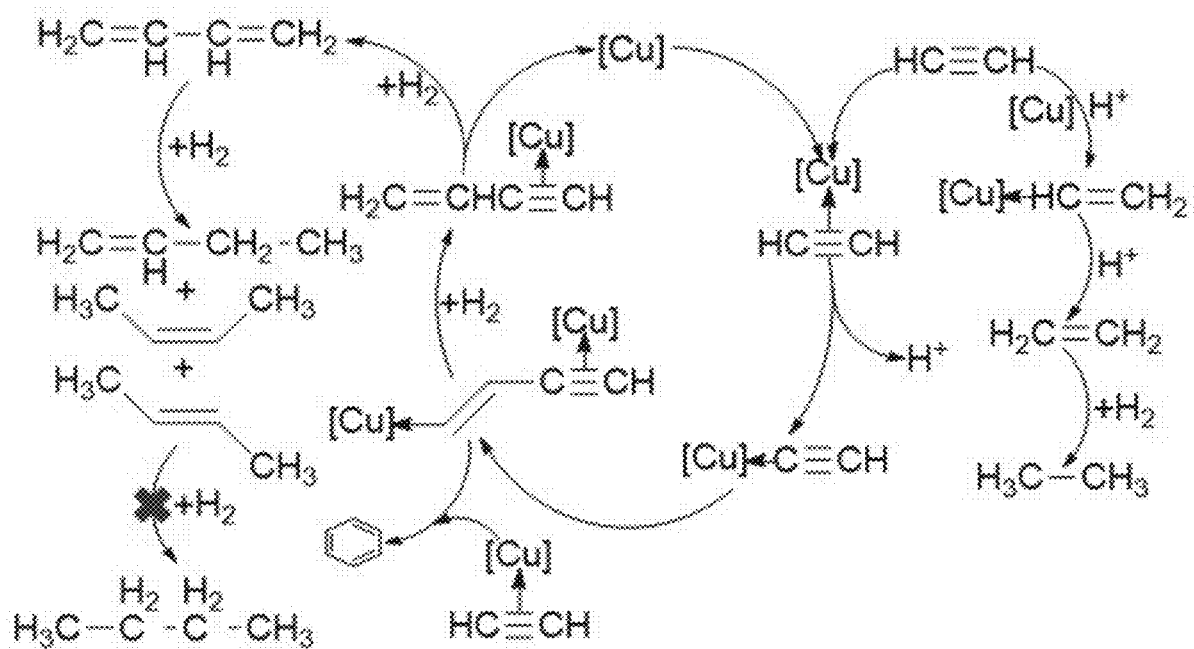
FIG. 9 shows a proposed reaction pathway for acetylene hydrodimerization over 10% Cu/MOR catalyst.

Based on the experimental results and literature reports, a reaction pathway over 10% Cu/MOR catalyst is postulated and illustrated in FIG. 9, where [Cu] represents the active sites of 10% Cu/MOR catalyst. Previous reports show that dimerization of acetylene is initiated with the formation of [Cu]—$C_2H_2$ π-complex, then a proton is dissociated from the [Cu]—$C_2H_2$ π-complex to form a [Cu]—$C_2H_2$ σ-complex. The [Cu]—$C_2H_2$ σ-complex, [Cu]—$C_2H_2$ σ-complex can rapidly react to form the $C_4$ intermediates under a hydrogen atmosphere. Interestingly, for conventional Nieuwland catalyst, the monovinylacetylene (MVA) could be obtained immediately after the $C_4$ intermediates are formed under the liquid media. However, for the reaction system in this study, MVA was not observed. Instead, 1,3-butadiene is produced. The absence of MVA tends to indicate that the [Cu]—$C_2H_2$ intermediate and vinyl intermediate ([Cu]←CH=CH$_2$) are formed in parallel, leading to $C_4$ formation and $C_2$ formation, respectively. Additionally, t-2-butene, 1-butene, and c-2-butene are also obtained in the reaction. This is mainly due to the subsequent hydrogenation of 1,3-butadiene in the presence of hydrogen. Moreover, ethylene and ethane are produced from hydrogenation of acetylene. The dissociated hydrogen and acetylene react to form a vinyl intermediate ([Cu]←CH=CH$_2$) on the surface of catalyst. The vinyl intermediate then accepts protons to form ethylene and ethane under the hydrogen atmosphere. The formation of benzene undergoes trimerization of acetylene. As literature reported, the HCC angle became less than 180° due to the linear structure of acetylene molecules adsorbed on the Cu catalyst, then two acetylene molecules could dimerize after the adsorption to form $C_4H_4$ intermediate. The dimerization process is exothermic by 1.29 eV and exhibits a barrier about 0.77 eV. In order to form a benzene molecule, the $C_4H_4$ intermediate will need to rotate and transform to a configuration that is sterically favored for the combination with the third acetylene molecule to form a benzene molecule.

FIG. 10 shows the time-on-stream conversion of acetylene over 10% Cu/MOR catalyst and the characterization of the spent catalyst. Though the conversion of acetylene gradually decreases as reaction proceeds, it remains steady at conversion level of ~93% during a 6 h test (FIG. 10A) and the selectivities for $C_2$, $C_4$, and benzene are also very stable during this process.

Figure 10A:
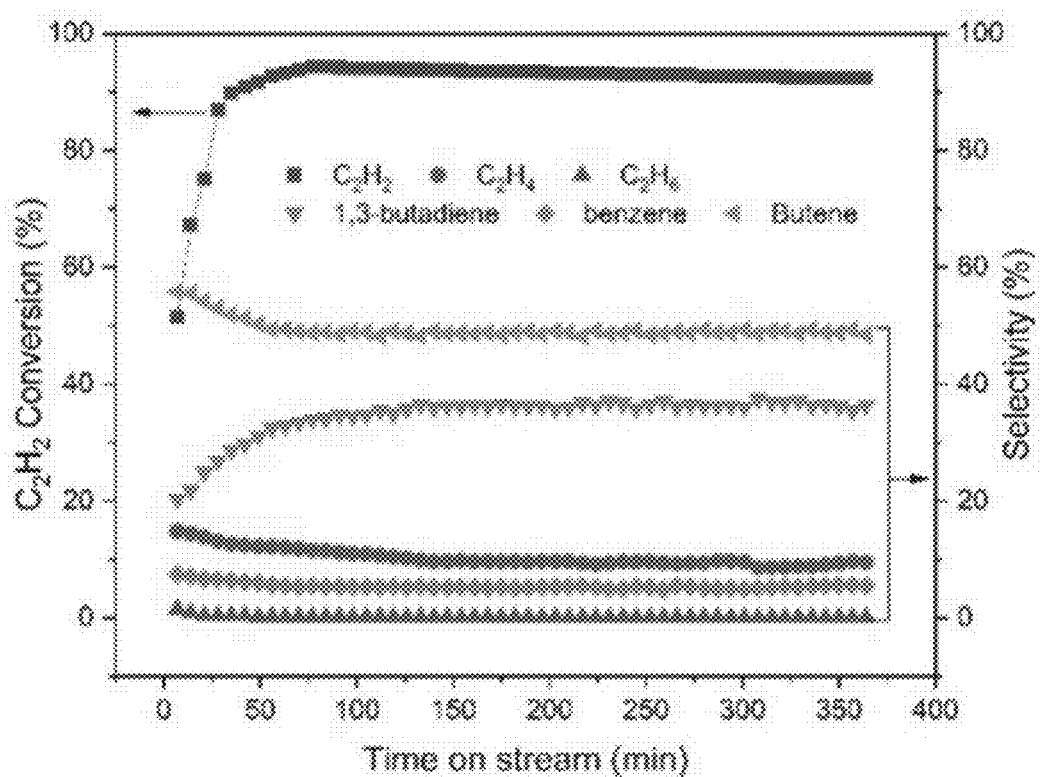
FIGS. 10A-10D show representative stability data of 10% Cu/MOR catalyst and characterization of spent catalyst.
Figure 10B:
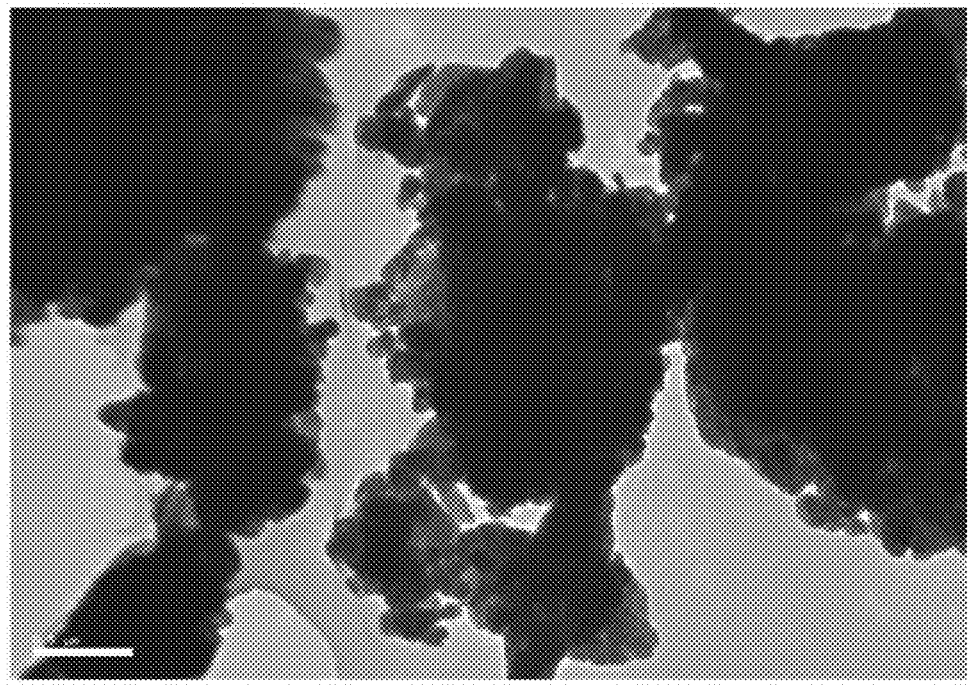
Figure 10C:
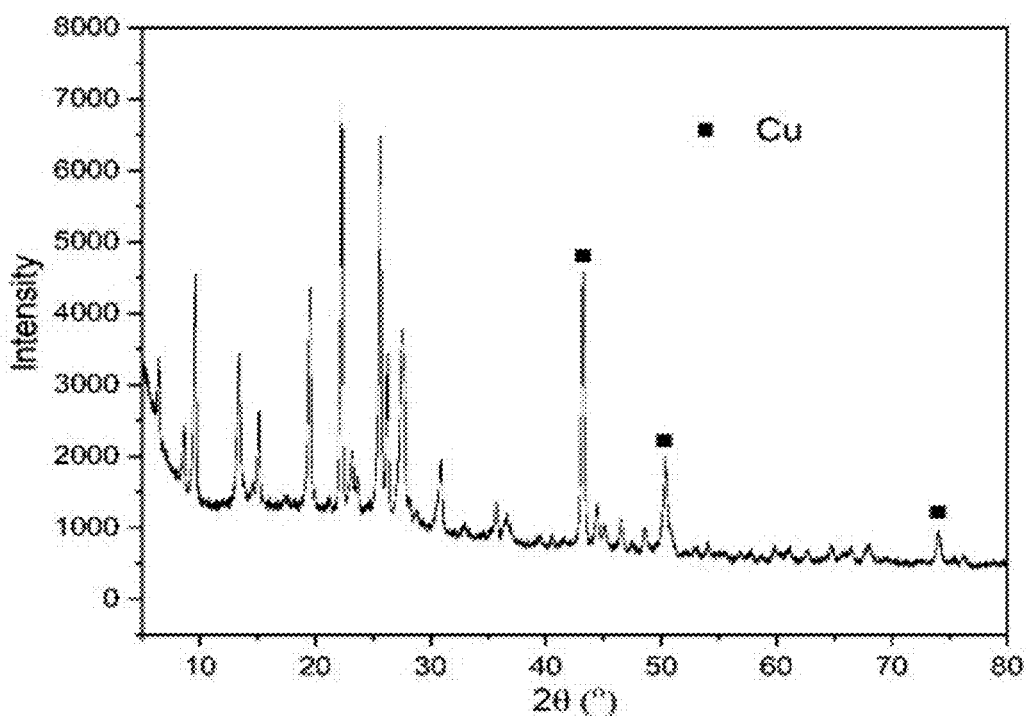
Figure 10D:
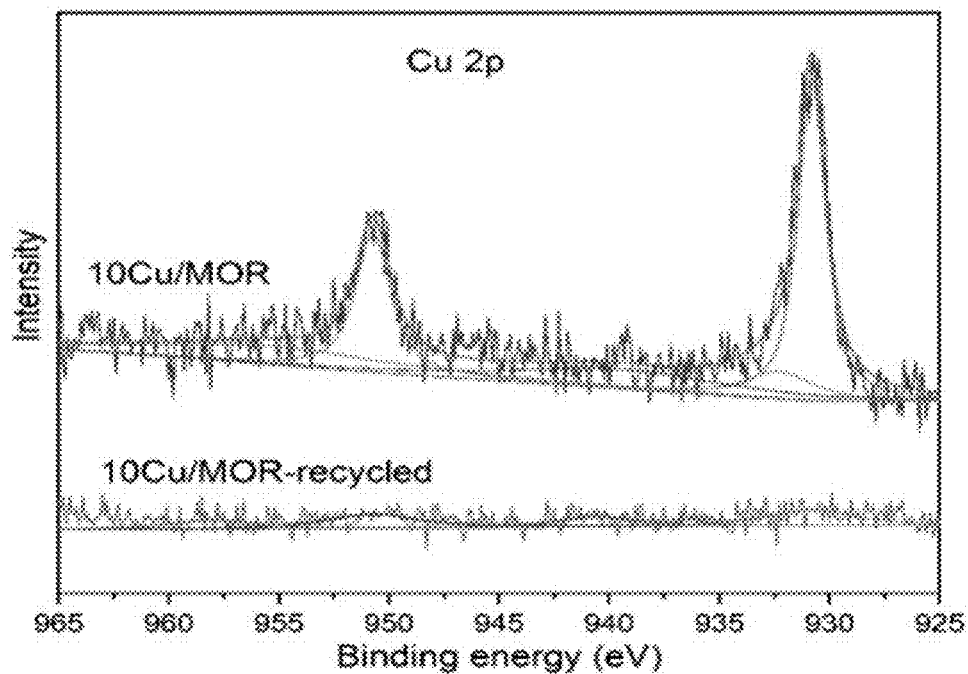

FIG. 10B shows that small copper particles are still observed on the surface of the spent catalyst. In addition, the copper diffraction peaks at 43.30°, 50.43°, and 74.13° on the spent 10 wt % Cu/MOR catalyst in FIG. 10C indicates the stable structure of the catalyst in the reaction system. In order to further confirm the chemical composition of 10 wt % Cu/MOR catalyst before and after reaction, XPS measurements were performed and the Cu 2p XPS spectra are shown in FIG. 10D. Two sharp peaks are observed at 933.8 eV and 953.7 eV for the fresh 10 wt % Cu/MOR catalyst, with a spin-energy separation of 19.9 eV, which can be attributed to the binding energy of Cu $2p_{3/2}$ and Cu $2p_{1/2}$. Generally speaking, there are two kinds of $Cu^{2+}$ in the catalyst: isolated $Cu^{2+}$ (also known as highly dispersed copper oxide species or small two- and three-dimensional clusters) and bulk copper oxide. The deconvoluted small peaks at 935.4 and 958 eV are related to $Cu^{2+}$, indicating that $Cu^{2+}$ species are coordinated with oxygen atoms and agglomerated with the CuO clusters. Furthermore, the peak around 940 eV is related to the bulk copper oxide on the surface of MOR, which can be seen from TEM morphology in FIG. 3C. For the spent 10 wt % Cu/MOR catalyst, the sharp peaks observed at 933.8 eV and 953.7 eV become very low compared to that for the fresh catalyst. This may be due to the formation of CH species on the surface of catalyst, which limits Cu measurement by XPS.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:
1. A method for producing $C_4$ olefins from acetylene, the method comprising:
 a. placing a catalyst in a reactor;
 b. providing a flow of feed gas through the reactor;
 c. reacting the feed gas at a first temperature for a first period of time to produce a product mixture; and
 d. collecting the product mixture;
 wherein the catalyst comprises a first metal;
  wherein the first metal is selected from Cu, Fe, Co, Ni, Pd, Pt, Rh, and combinations thereof; and
  wherein the first metal is present in an amount from about 5 wt % to about 15 wt %:
 wherein the catalyst comprises a promoter;
  wherein the promoter comprises a second metal;
  wherein the second metal is selected from Ru, Ga, Ag, and combinations thereof; and wherein the second metal is present in an amount from about 0.05 wt % to about 10 wt %;
wherein the catalyst further comprises a catalyst support;
wherein the catalyst support is selected from a material comprising $SiO_2$, $Al_2O_3$, $ZrO_2$, $TiO_2$, $CeO_2$, a zeolite, ammonium zeolite mordenite, and combinations thereof;
wherein the feed gas comprises acetylene; and
wherein the product mixture comprises at least one $C_4$ olefin.

2. The method of claim 1, wherein the first metal comprises Cu.

3. The method of claim 1, the catalyst support comprises ammonium zeolite mordenite.

4. The method of claim 3, wherein the ammonium zeolite mordenite comprises $SiO_2$ and $Al_2O_3$ in a mole ratio of from about 10:1 to about 30:1 mole ratio.

5. The method of claim 1, wherein the first metal comprises copper in an amount of from about 7.5 wt % to about 12.5 wt % of the total weight of the catalyst and the catalyst support.

6. The method of claim 1, wherein the promoter is present in an amount of from about 0.5 wt % to about 2 wt % of the total weight of the catalyst and the catalyst support.

7. The method of claim 1, wherein the first metal comprises copper in an amount of 10 wt % of the total weight of the catalyst and the catalyst support, the second metal comprises ruthenium in an amount of from about 0.1 wt % to about 1 wt % of the total weight of the catalyst and the catalyst support, and the catalyst support comprises ammonium zeolite mordenite.

8. The method of claim 1, wherein the first metal comprises copper in an amount of 10 wt % of the total weight of the catalyst and the catalyst support, the second metal comprises gallium in an amount of 1 wt % of the total weight of the catalyst and the catalyst support, and the catalyst support comprises ammonium zeolite mordenite.

9. The method of claim 1, wherein the feed gas comprises acetylene and hydrogen.

10. The method of claim 9, wherein the feed gas comprises from about 5 to about 95 vol % acetylene.

11. The method of claim 9, wherein the feed gas comprises a molar ratio of hydrogen to acetylene of from about 2:1 to about 8:1.

12. The method of claim 9, wherein the feed gas comprises a pressure of about 1-200 psig.

13. The method of claim 1, wherein the first temperature is from about 150° C. to about 300° C.

14. The method of claim 1, wherein the at least one $C_4$ olefin comprises 1-butene, cis-2-butene, trans-2-butene, 1,3-butadiene, or a combination thereof.

15. The method of claim 1, wherein the product mixture comprises at least 80 mol % $C_4$ olefins.

16. The method of claim 1, wherein the product mixture further comprises at least one value-added product.

17. The method of claim 16, wherein the at least one value-added product comprises ethylene, benzene, or a combination thereof.

18. The method of claim 17, wherein the product mixture comprises from about 3 mol % to about 8 mol % benzene; and wherein the product mixture comprises from about 5 mol % to about 25 mol % ethylene.

19. The method of claim 9, wherein conversion of acetylene is about 100%.

20. The method of claim 1, wherein the catalyst support is selected from $Al_2O_3$, a zeolite, ammonium zeolite mordenite, and combinations thereof.

21. A composition comprising a hydrocarbon produced by the method of claim 1.

22. An article comprising the composition of claim 21.

* * * * *